(12) United States Patent
Chun et al.

(10) Patent No.: US 12,053,207 B2
(45) Date of Patent: Aug. 6, 2024

(54) LOADING TOOL FOR A BIOSTIMULATOR

(71) Applicant: Pacesetter, Inc., Sylmar, CA (US)

(72) Inventors: Byron Liehwah Chun, San Francisco, CA (US); Sondra Orts, Sunnyvale, CA (US); Thomas B. Eby, Mountain View, CA (US); Stephanie M. Raymond, Porter Ranch, CA (US); Mike Sacha, Chanhassen, MN (US); Bernhard Arnar, Minnetrista, MN (US); Adam Weber, Minnetonka, MN (US); Jennifer Heisel, Princeton, MN (US); Wade Keller, Aliso Viejo, CA (US)

(73) Assignee: PACESETTER, INC., Sylmar, CA (US)

( * ) Notice: Subject to any disclaimer, the term of this patent is extended or adjusted under 35 U.S.C. 154(b) by 1148 days.

(21) Appl. No.: 16/359,703

(22) Filed: Mar. 20, 2019

(65) Prior Publication Data

US 2019/0290323 A1 Sep. 26, 2019

Related U.S. Application Data

(60) Provisional application No. 62/665,281, filed on May 1, 2018, provisional application No. 62/645,928, filed on Mar. 21, 2018.

(51) Int. Cl.
*A61B 17/34* (2006.01)
*A61N 1/372* (2006.01)
(Continued)

(52) U.S. Cl.
CPC ......... *A61B 17/3468* (2013.01); *A61N 1/372* (2013.01); *A61B 2017/00292* (2013.01);
(Continued)

(58) Field of Classification Search
CPC ...... A61B 17/3468; A61B 2017/00292; A61B 2017/00477; A61B 2017/12054;
(Continued)

(56) References Cited

U.S. PATENT DOCUMENTS 5,819,971 A * 10/1998 Tseng ................... B65D 43/163
220/4.23
6,132,458 A * 10/2000 Staehle ..................... A61F 2/95
623/1.11
(Continued)

FOREIGN PATENT DOCUMENTS

EP 3377173 9/2018
WO 2007/047681 A2 4/2007
(Continued)

OTHER PUBLICATIONS

NonFinal Office Action—mailed on Jan. 15, 2019; U.S. Appl. No. 15/497,675.

*Primary Examiner* — Diane D Yabut
(74) *Attorney, Agent, or Firm* — WOMBLE BOND DICKINSON (US) LLP

(57) ABSTRACT

A loading tool for loading a biostimulator onto a biostimulator delivery system is described. The loading tool includes a first body portion and a second body portion connected by a hinge. A latch is mounted on the first body portion, and the latch can be locked to fasten the first body portion to the second body portion. A biostimulator can be mounted in the loading tool, and a tether of a biostimulator delivery system can be inserted through a funnel in the loading tool to engage the biostimulator. An operator can use only one hand to unlock the latch, open the loading tool, and remove the loading tool from the biostimulator prior to delivering the biostimulator into a patient. Other embodiments are also described and claimed.

14 Claims, 22 Drawing Sheets

(51) Int. Cl.
*A61B 17/00* (2006.01)
*A61N 1/362* (2006.01)
*A61N 1/375* (2006.01)

(52) U.S. Cl.
CPC ..... *A61B 2017/00477* (2013.01); *A61N 1/362* (2013.01); *A61N 1/3756* (2013.01)

(58) Field of Classification Search
CPC ...... A61N 1/362; A61N 1/372; A61N 1/3756; B65D 43/22; B65D 2251/1058; B65D 2543/00879; B65D 2543/0087; B65D 2543/00861; B65D 2543/00851; B65D 2543/00842; B65D 2543/00833; B65D 5/665; B65D 55/02; B65D 55/10; B65D 2251/1016; B65D 2555/02; A61F 2/0095; A45D 2040/223; E05B 65/5223; E05B 65/5215; E05B 65/5238; E05B 65/523; A61M 25/0631; A61M 25/002
See application file for complete search history.

(56) References Cited

U.S. PATENT DOCUMENTS

| | | | |
|---|---|---|---|
| 6,186,325 B1 | 2/2001 | Schmidt et al. | |
| 6,357,589 B2 | 3/2002 | Schmidt et al. | |
| 6,439,276 B1* | 8/2002 | Wood | A61M 5/3205 141/97 |
| 6,616,635 B1* | 9/2003 | Bell | A61M 25/0631 604/263 |
| 9,120,605 B1* | 9/2015 | Mar | B65D 43/162 |
| 2001/0037954 A1 | 11/2001 | Schmidt et al. | |
| 2002/0096517 A1* | 7/2002 | Gelardi | B65D 43/22 220/4.23 |
| 2005/0218022 A1* | 10/2005 | Cervantes | A61F 2/0095 623/1.11 |
| 2005/0252805 A1* | 11/2005 | Cervantes | A61F 2/0095 206/384 |
| 2007/0088394 A1 | 4/2007 | Jacobson | |
| 2007/0088396 A1 | 4/2007 | Jacobson | |
| 2007/0088397 A1 | 4/2007 | Jacobson | |
| 2007/0088398 A1 | 4/2007 | Jacobson | |
| 2007/0088400 A1 | 4/2007 | Jacobson | |
| 2007/0088405 A1 | 4/2007 | Jacobson | |
| 2007/0088418 A1 | 4/2007 | Jacobson | |
| 2008/0086192 A1* | 4/2008 | WasDyke | A61F 2/0095 623/1.12 |
| 2008/0221703 A1 | 9/2008 | Que et al. | |
| 2009/0076585 A1 | 3/2009 | Hendriksen et al. | |
| 2012/0083874 A1* | 4/2012 | Dale | A61F 2/2427 623/2.11 |
| 2012/0197373 A1 | 8/2012 | Khairkhahan et al. | |
| 2014/0207175 A1 | 7/2014 | Aggerholm | |
| 2015/0051609 A1 | 2/2015 | Schmidt et al. | |
| 2016/0128819 A1 | 5/2016 | Giordano et al. | |
| 2016/0243355 A1 | 8/2016 | Wood | |
| 2016/0270914 A1 | 9/2016 | Krans et al. | |
| 2017/0119999 A1 | 5/2017 | Kelly | |
| 2017/0136231 A1 | 5/2017 | Kelly et al. | |
| 2017/0143955 A1 | 5/2017 | Soltis et al. | |
| 2017/0158396 A1* | 6/2017 | Guirguis | B65D 50/00 |
| 2017/0319847 A1* | 11/2017 | Ho | A61N 1/362 |
| 2018/0050209 A1 | 2/2018 | Raines | |
| 2018/0117304 A1 | 5/2018 | Koop et al. | |
| 2018/0140855 A1 | 5/2018 | Kane et al. | |
| 2018/0178006 A1 | 6/2018 | Soltis et al. | |
| 2018/0178007 A1 | 6/2018 | Shuros et al. | |

FOREIGN PATENT DOCUMENTS

| | | |
|---|---|---|
| WO | 2017074553 A1 | 5/2017 |
| WO | 2017087661 A1 | 5/2017 |
| WO | 2018081225 A1 | 5/2018 |
| WO | 2018136203 A1 | 7/2018 |

* cited by examiner

LOADING TOOL FOR A BIOSTIMULATOR

This application claims the benefit of priority of U.S. Provisional Patent Application No. 62/645,928, filed on Mar. 21, 2018, and U.S. Provisional Patent Application No. 62/665,281, filed on May 1, 2018, which are incorporated herein by reference in their entirety to provide continuity of disclosure.

BACKGROUND

Field

The present disclosure relates to biostimulators and related delivery systems and methods. More specifically, the present disclosure relates to devices and methods for loading a leadless cardiac pacemaker onto a pacemaker delivery system.

Background Information

Artificial pacemakers provide an electrical stimulation to the heart to perform cardiac pacing when a conduction system of the heart fails to naturally provide synchronized atrial and ventricular contractions at rates and intervals sufficient for a patient's health. Such antibradycardial pacing provides relief from symptoms and even life support for hundreds of thousands of patients.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The pulse generator usually connects to one or more implanted leads, the distal end(s) of which contain one or more electrodes for positioning adjacent to the inside or outside wall of a cardiac chamber. The leads have an insulated electrical conductor or conductors for connecting the pulse generator to electrodes in the heart. The leads typically have lengths of 50 to 70 centimeters.

Conventional pacemakers have several drawbacks, including pulse generators that, when located subcutaneously, present a bulge in the skin that patients can find unsightly, unpleasant, or irritating. Furthermore, conventional pacemakers have complex connections to the leads that can malfunction. Other problematic aspects of conventional pacemakers relate to the separately implanted pulse generator and the pacing leads. By way of example, the pacing leads can become a site of infection and morbidity.

Many of the issues associated with conventional pacemakers are resolved by a self-contained and self-sustainable pacemaker, or so-called leadless pacemaker. Similar to active fixation implantable leads used with conventional pulse generators, leadless pacemakers are typically fixed to an intracardial implant site by an actively engaging mechanism such as a helical member that screws into the myocardium. Leadless pacemakers are typically delivered to an intracardial implant site via a delivery system including catheters, sheaths and/or introducers. Such leadless pacemakers are typically preloaded onto the delivery system during manufacturing and then packaged and sterilized in that preloaded configuration.

SUMMARY

Biostimulators, e.g., leadless cardiac pacemakers, that are packaged and preloaded on a delivery system can present several issues. For example, if the physician needs to implant multiple biostimulators into the patient, as may be the case in a dual chamber cardiac pacing arrangement, the physician would require two separate preloaded delivery systems to deliver both biostimulators. Also, if the biostimulator is damaged during the course of the procedure, but the delivery system is still functional, the physician would need to open a new preloaded delivery system in order to complete the procedure. Finally, sterilization cycles, shelf life, distribution, and inventory management are complicated by having the biostimulator joined to the delivery system in manufacturing. All of the forgoing result in significant waste and additional cost associated with each implantation procedure.

A loading tool for loading a biostimulator onto a biostimulator delivery system in a clinical setting is provided. The loading tool can include a first body portion hinged to a second body portion such that the body portions can open and close relative to each other. The loading tool includes a latch mounted on the first body portion, and the latch can engage a keeper of the second body portion. For example, the keeper can receive the latch to hold the first body portion against the second body portion. The latch can be slidably mounted on the first body portion or hinged to the first body portion. Accordingly, the latch can be locked by sliding a latch tooth under a ledge of the keeper or pivoting the latch tooth under the ledge. To open the latch, an operator can use one hand to pivot or slide the latch to an unlocked configuration. Accordingly, the loading tool can provide an easy-to-use solution for loading a biostimulator onto a biostimulator delivery system in the clinical setting.

A biostimulator system includes a biostimulator, e.g., a leadless cardiac pacemaker, mounted in the loading tool. More particularly, the biostimulator can be mounted in a loading volume of the loading tool. The loading volume can be defined by a combination of a first recess in the first body portion and a second recess in the second body portion. When the loading tool is closed, and the first body portion is locked against the second body portion by the latch, the loading volume holds the biostimulator. The loading volume can include subvolumes, such as a biostimulator volume to hold the biostimulator and a catheter volume to receive a distal end of a biostimulator delivery system. In an embodiment, the loading volume also includes a funnel volume tapering from the catheter volume to the biostimulator volume. Accordingly, the biostimulator system can provide a loading tool preloaded with a biostimulator for attachment to a biostimulator delivery system in the clinical setting.

A method of loading the biostimulator, e.g., the biostimulator, onto the biostimulator delivery system includes inserting the distal end, e.g., a docking cap, of the biostimulator delivery system into the catheter volume of the loading tool. When the biostimulator delivery system is docked in the catheter volume, a tether of the biostimulator delivery system can pass through the funnel volume into the biostimulator volume. More particularly, the tether can insert into an opening of the biostimulator to connect the biostimulator to the biostimulator delivery system. After the connection is made, an operator can unlock the latch of the loading tool. For example, the operator can single-handedly slide or press on a latch tab to cause the latch to unfasten the first body portion and the second body portion. In the unlatched configuration, the first body portion can swing about a hinge, e.g., by pinching wing tabs of the loading tool, to separate the first body portion from the second body portion such that the loading volume is opened. The loading tool can be removed from the biostimulator and the biostimulator delivery system using one hand, and the biostimulator can be docked to the biostimulator delivery system for delivery into a patient.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

Figure 1:
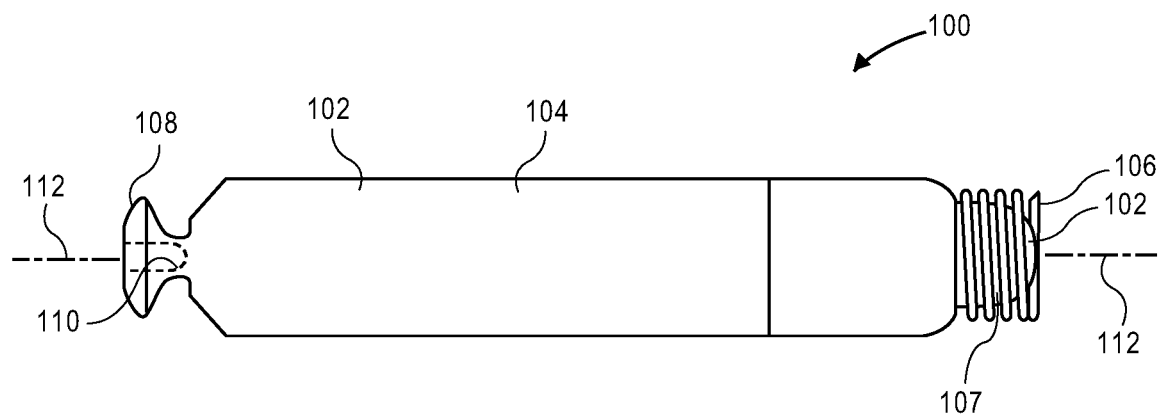
FIG. 1 is a side view of a biostimulator, in accordance with an embodiment.

Embodiments describe a loading tool and method for loading a biostimulator, such as a leadless cardiac pacemaker, onto a delivery system. The loading tool can be used in a catheterization laboratory to load the biostimulator onto the biostimulator delivery system prior to implantation into a patient. The loading tool, however, may be used in other applications, such as in a manufacturing setting to load the biostimulator onto the biostimulator delivery system prior to shipment to the customer.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "proximal" may indicate a first direction along a central axis of a loading tool. Similarly, "distal" may indicate a second direction opposite to the first direction. Such terms are provided to establish relative frames of reference, however, and are not intended to limit the use or orientation of a loading tool to a specific configuration described in the various embodiments below.

Loading tools used to load a biostimulator onto a biostimulator delivery system can be opened after connecting a tether of the biostimulator delivery system to the biostimulator. The opening can include unlocking a locking mechanism that holds a first half of the loading tool to a second half, and then separating the halves to release a biostimulator contained between the halves. Currently, the opening process can require an operator to use both hands to unlock the locking mechanism. While the operator is using both hands, the biostimulator delivery system can dangle from the loading tool by the tether, and damage to the biostimulator delivery system may occur. For example, the tether or a catheter component of the biostimulator delivery system may kink under a weight of other system components, such as the biostimulator.

In an aspect, a loading tool can improve ease-of-use for the operator by facilitating one-handed opening of the loading tool to release the biostimulator after it is connected to the biostimulator delivery system. The single-handed operation can be facilitated by a latch mounted on the loading tool body. The latch can be easily opened by a pivoting or sliding action using one hand. Opening of the body portion can be further facilitated by wing tabs that the operator can pinch or flip to easily open the unlatched loading tool. Accordingly, the loading tool can be loaded with a biostimulator, docked to the biostimulator delivery system, and unlocked/removed with one hand, which simplifies the loading process and reduces a likelihood of damage to the biostimulator delivery system.

In an aspect, a loading tool can include a docking feature to receive and support a distal end of a biostimulator delivery system during the loading process. The docking feature can be a guide barrel that the biostimulator delivery system can be inserted into. The guide barrel can have a wall that conforms to an outer surface of the biostimulator delivery system, and thus, can resist lateral displacement of the biostimulator delivery system. This support can reduce a likelihood that a tether or catheter component of the biostimulator delivery system will become kinked or damaged. The guide barrel can include other features to support and retain the biostimulator delivery system during the loading process. For example, the loading tool can include a detent extending from the guide barrel to resist proximal movement of the biostimulator delivery system when the system is docked in the guide barrel. Accordingly, the biostimulator delivery system can be safely supported by the guide barrel until the operator unlatches the loading tool and removes it from the biostimulator and biostimulator delivery system.

Biostimulator and Biostimulator Delivery System

Referring to FIG. 1, a side view of a biostimulator is shown in accordance with an embodiment. A biostimulator 100, such as a leadless cardiac pacemaker, can perform cardiac pacing that has many of the advantages of conventional cardiac pacemakers while extending performance, functionality, and operating characteristics with one or more of several improvements. In some embodiments of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

The biostimulator 100 can have two or more electrodes 102 located within, on, or near a housing 104, for delivering pacing pulses to muscle of the cardiac chamber and optionally for sensing electrical activity from the muscle, and for bidirectional communication with at least one other device within or outside the body. The housing 104 can contain a primary battery (not shown) to provide power for pacing, sensing, and communication, for example bidirectional communication. The housing 104 can optionally contain circuits for sensing cardiac activity from the electrodes 102. The housing 104 contains circuits for receiving information from at least one other device via the electrodes 102 and contains circuits for generating pacing pulses for delivery via the electrodes 102. The housing 104 can optionally contain circuits for transmitting information to at least one other device via the electrodes 102 and can optionally contain circuits for monitoring device health. The housing 104 contains circuits for controlling these operations in a predetermined manner.

The biostimulator 100 can include an anchor 106 mounted on the housing 104. For example, the anchor 106 can be mounted on an anchor mount 107 extending from a distal end of the biostimulator 100. The biostimulator 100 may also include an attachment feature. The attachment feature may be, for example, a docking button 108 having an opening 110 extending along a central axis 112 of the biostimulator 100. The opening 110 can be sized to receive tethers of a biostimulator delivery system, as described below. The docking button 108 can be connected to, and proximally spaced-apart from, a proximal end of the housing 104. The anchor 106 is operably connected to a distal end of the housing 104.

Figure 2:
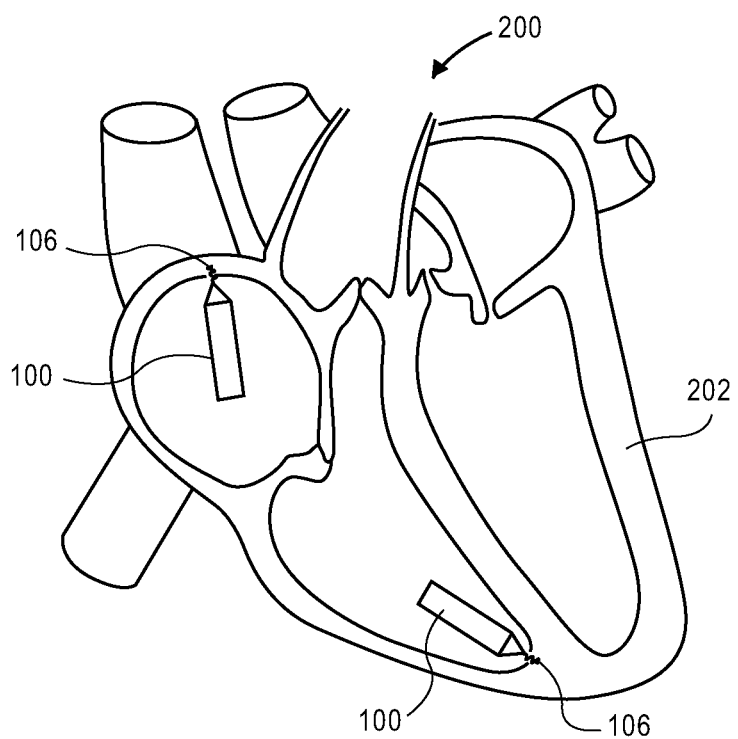
FIG. 2 is a pictorial view of a biostimulator implanted in a patient heart, in accordance with an embodiment.

Referring to FIG. 2, a pictorial view of a biostimulator implanted in a patient heart is shown in accordance with an embodiment. A cardiac pacing system 200 includes one or more biostimulators 100. Each biostimulator 100 is suitable for placement on, or attachment to, the inside or outside of a cardiac chamber, such as a right atrium and/or right ventricle of the patient heart 202. Attachment of the biostimulators 100 to the cardiac tissue can be accomplished via the anchor 106 of the biostimulator 100.

Biostimulators 100 can be delivered to and retrieved from a patient using any of the delivery systems described herein. In some embodiments, a biostimulator 100 is attached or connected to a biostimulator delivery system and advanced intravenously into the heart 202. The biostimulator delivery system can include features to engage the biostimulator 100 to allow fixation of the biostimulator 100 to tissue. For example, in embodiments where the biostimulator 100 includes an active engaging anchor 106, such as a screw or helical member, the delivery system can transmit torque to the biostimulator 100 to screw the active engaging mechanism into the tissue.

Figure 3:
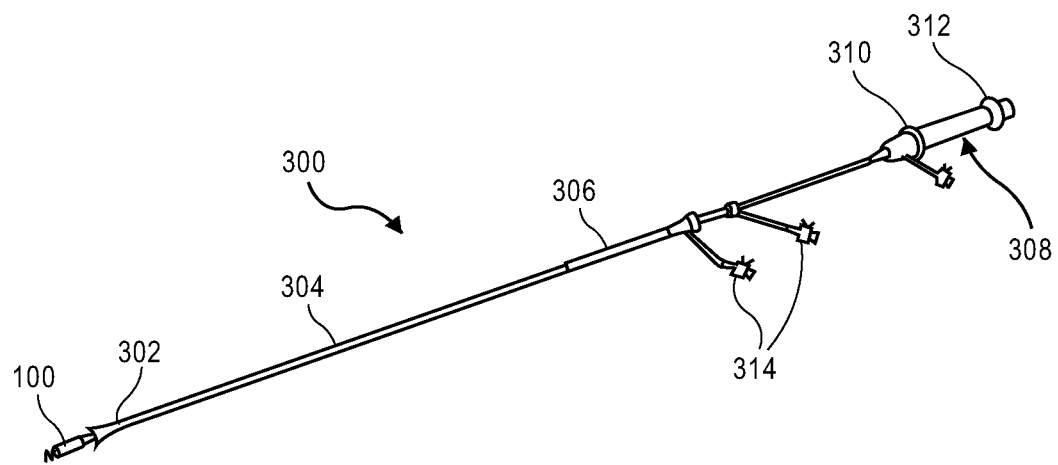
FIG. 3, is a perspective view of a biostimulator loaded onto a biostimulator delivery system, in accordance with an embodiment.

Referring to FIG. 3, a perspective view of a biostimulator loaded onto a biostimulator delivery system is shown in accordance with an embodiment. A biostimulator delivery system 300 can include a biostimulator sheath 302, a guide catheter shaft 304, an introducer hub assembly 306, a handle 308, a deflection knob 310, a tether shuttle 312, and flush ports 314. The deflection knob 310 can be used to steer and guide a deflectable catheter during implantation and/or removal of the biostimulator 100. The flush ports 314 can be used to flush saline or other fluids through the catheter. The introducer hub assembly 306 can be advanced distally over the catheter shaft 304 to provide additional steering and support for the delivery catheter during implantation and to surround the biostimulator 100 as it is introduced through a trocar or introducer into the patient.

Figure 4:
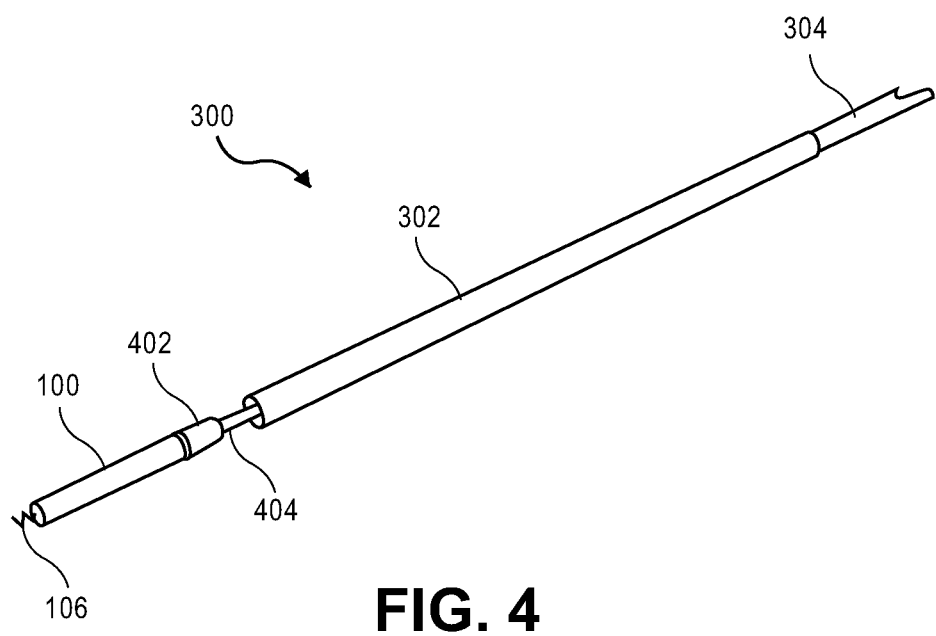
FIG. 4 is a perspective view of a distal portion of a biostimulator delivery system carrying a biostimulator, in accordance with an embodiment.

Referring to FIG. 4, a perspective view of a distal portion of a biostimulator delivery system carrying a biostimulator is shown in accordance with an embodiment. The biostimulator 100 can be attached to a docking cap 402 of the biostimulator delivery system 300. The docking cap 402 can be coupled to a distal end of the deflectable catheter 404. The biostimulator sheath 302 can be moved axially, e.g., extended distally or retracted proximally, along the deflectable catheter 404 to protect or expose the biostimulator 100 and/or the anchor 106. More particularly, the guide catheter shaft 304 can be advanced or retracted to cover or expose the biostimulator 100 to a surrounding environment. When the biostimulator sheath 302 is pulled back proximally, the biostimulator 100 is in an exposed, delivery configuration. When the biostimulator sheath 302 is advanced distally to protect the biostimulator 100 and anchor 106, the biostimulator 100 is in a protected, advancement configuration. During initial insertion of the biostimulator delivery system 300 into a patient, a physician can gain access to the patient's vascular system with the introducer hub assembly 306. The biostimulator 100 and the deflectable catheter 404 can then be advanced through the introducer hub assembly 306 (while covered by the biostimulator sheath 302) into the patient's vascular system to facilitate delivery of the biostimulator 100 into the heart 202.

Figure 5:
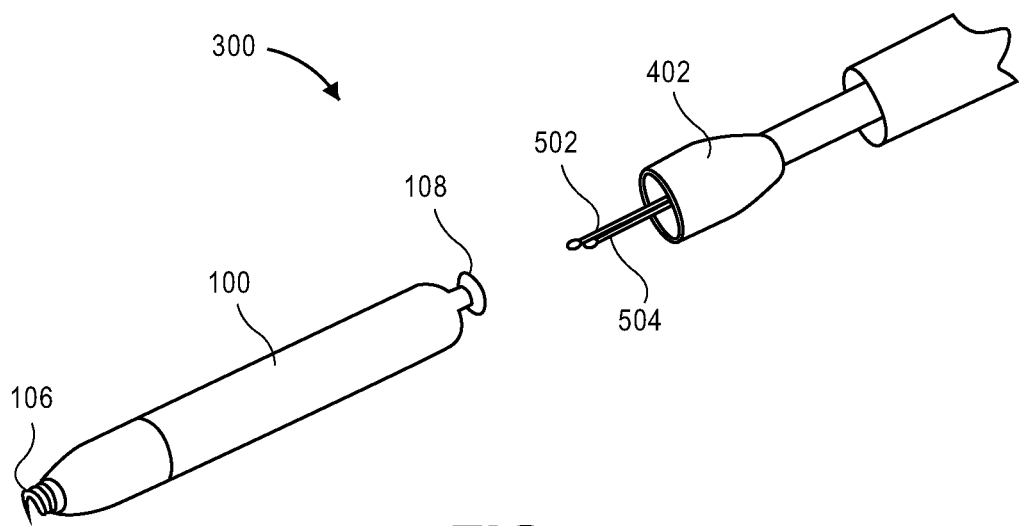
FIG. 5 is a perspective view of a biostimulator delivery system aligned with a biostimulator, in accordance with an embodiment.

Referring to FIG. 5, a perspective view of a biostimulator delivery system aligned with a biostimulator is shown in accordance with an embodiment. The biostimulator delivery system 300 can include one or more tethers, e.g., a first tether 502 and a second tether 504. The tethers can comprise wires, shafts, tubes, cords, ropes, strings, or other similar structures that can extend throughout the deflectable catheter 404. In some embodiments, the tethers comprise a shape memory material, such as nitinol. In other embodiments, the tethers comprise stainless steel wires or braids. The tethers can include respective distal ends that are axially displaceable relative to the docking cap 402. When the distal ends are staggered, the tethers can be inserted into or removed from the opening 110 in the docking button 108. That is, the opening 110 of the docking button 108 can be sized to receive the distal ends of the tethers one at a time during the loading process, as described below. The tethers can also be removed from the docking button 108 to deploy the biostimulator 100 at a target anatomy. For example, removal of the tethers can detach the biostimulator 100 from the biostimulator delivery system 300 as shown in FIG. 5.

Figure 6:
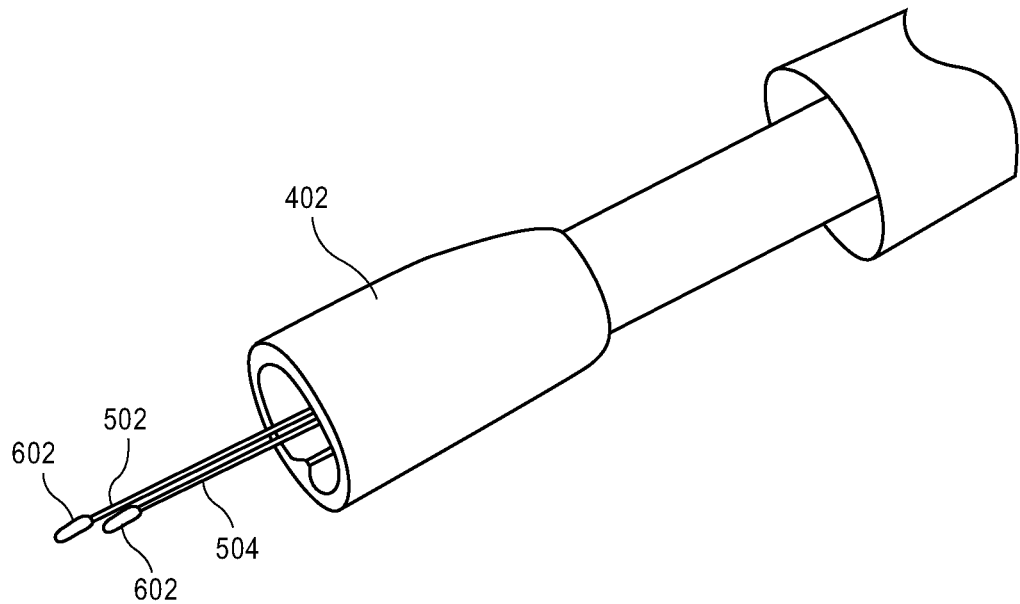
FIG. 6 is a perspective view of a distal portion of a biostimulator delivery system having misaligned tethers, in accordance with an embodiment.

Referring to FIG. 6, a perspective view of a distal portion of a biostimulator delivery system having misaligned tethers is shown in accordance with an embodiment. The tethers can include distal features 602. The distal features 602 can be, for example, features on the tethers that protrude radially from the tether, such as bumps, spheres, cylinders, rectangles, or other similar shapes extending outwards from the tethers. Generally, the distal features 602 have a cross sectional diameter larger than the cross sectional diameter of the tethers. As shown, in one embodiment, one of the distal feature 602 can be advanced further from the catheter than another distal feature 602, so that when the tethers are pushed together, one distal feature 602 rests against the first tether 502. A combined cross-sectional diameter of a distal feature 602 and a tether in the staggered configuration shown in FIG. 6 is less than a combined cross-sectional diameter of both distal features 602 as would be the case when the distal features 602 are aligned side by side, i.e., not staggered.

Figure 7:
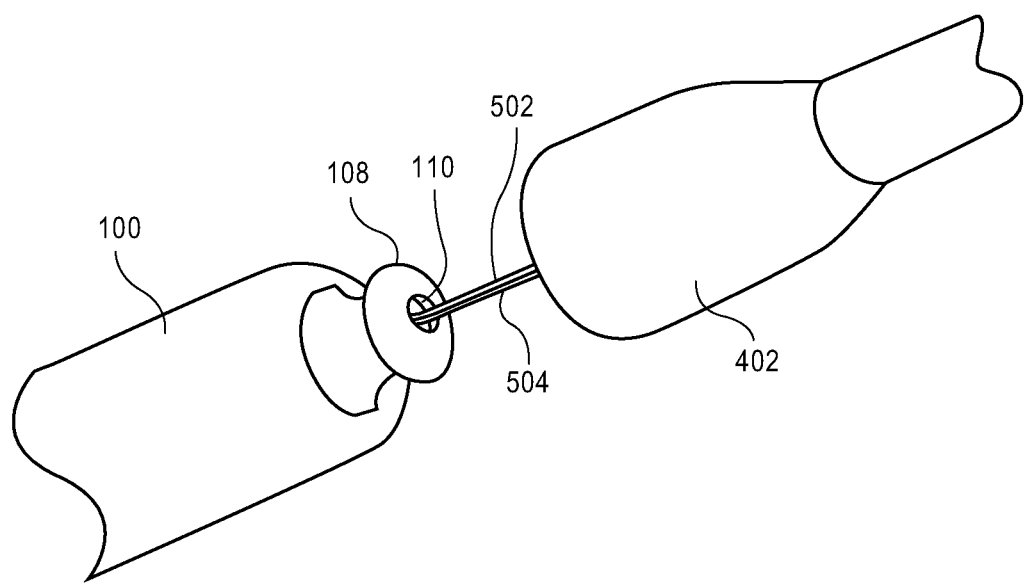
FIG. 7 is a perspective view of tethers of a biostimulator delivery system being inserted into a docking button of a biostimulator, in accordance with an embodiment.

Referring to FIG. 7, a perspective view of tethers of a biostimulator delivery system being inserted into a docking button of a biostimulator is shown in accordance with an embodiment. The length of the tethers, and thus the position of the distal features 602, can be adjusted so that the distal features are not aligned in a side by side configuration (e.g., the un-aligned configuration shown in FIGS. 5-6). For example, a tether adjustment feature can comprise knobs or dials on the handle 308, and a user can simply turn the knobs or dials to adjust the length of the tethers. When the tethers 502, 504 and distal features 602 are in the un-aligned configuration, the distal features can then be advanced through the opening 110 of the docking button 108. The opening 110 can be sufficiently large enough to allow the distal features 602 to pass one after the other when in the un-aligned configuration. Upon passing the distal features 602 through the opening 110, the length of the tethers can then be adjusted to align the distal features 602 in the side by side configuration. When the distal features 602 are positioned side by side, the combined cross sectional diameter of the distal features 602 becomes larger than the diameter of the opening 110, which essentially locks the tethers and distal features 602 in the docking button 108 to connect the biostimulator 100 to the biostimulator delivery system 300.

Figure 8:
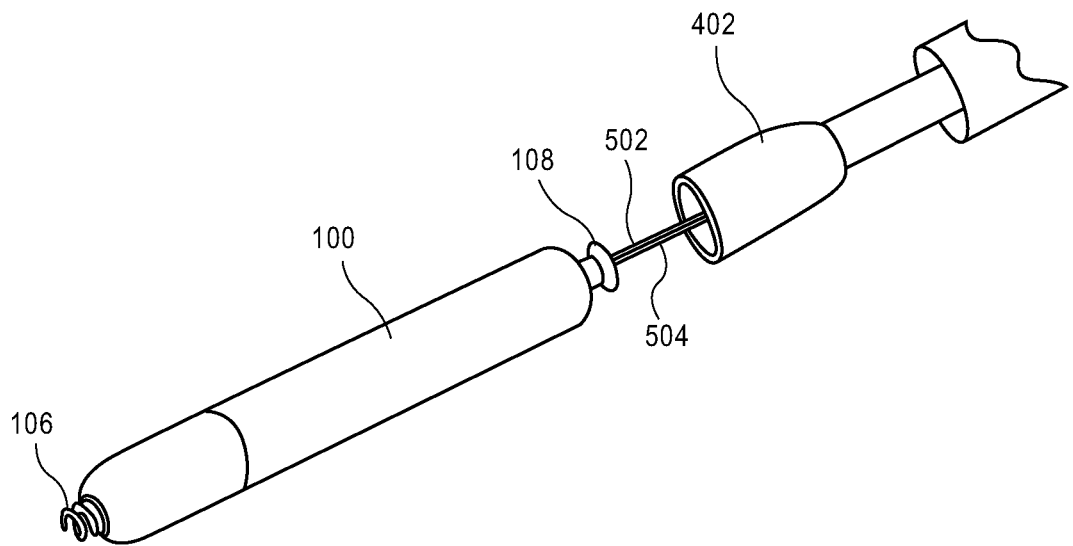
FIG. 8 is a perspective view of a biostimulator mounted on a biostimulator delivery system in an undocked configuration, in accordance with an embodiment.

Referring to FIG. 8, a perspective view of a biostimulator mounted on a biostimulator delivery system in an undocked configuration is shown in accordance with an embodiment. When the distal features 602 of the tethers are initially inserted into and locked in the docking button 108, the biostimulator 100 can be in an undocked configuration. The biostimulator 100 may be loosely attached to the biostimulator delivery system 300 by the tethers. More particularly, the biostimulator 100 may dangle from a distal end of the biostimulator delivery system 300 and the docking button 108 can be spaced apart from the docking cap 402.

Figure 9:
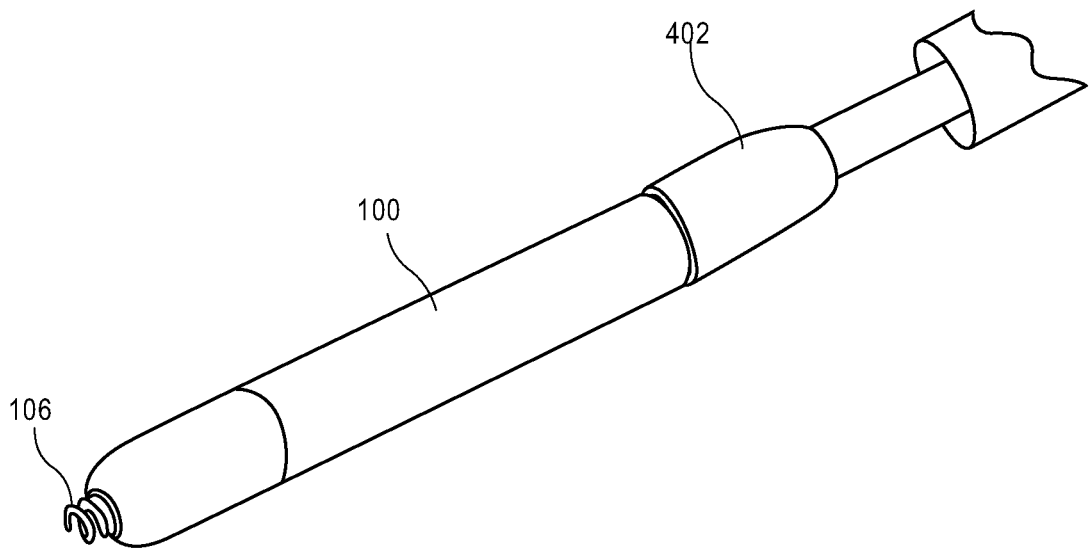
FIG. 9 is a perspective view of a biostimulator mounted on a biostimulator delivery system in a docked configuration, in accordance with an embodiment.

Referring to FIG. 9, a perspective view of a biostimulator mounted on a biostimulator delivery system in a docked configuration is shown in accordance with an embodiment. The docking button 108 of the biostimulator 100 can be docked in the docking cap 402 after locking the tethers through the opening 110. The tether shuttle 312 can be pulled proximally to cause the tethers to move proximally, thereby pulling the biostimulator 100 toward the biostimulator delivery system. When the biostimulator 100 is docked against the delivery system, e.g., when the docking button 108 is pulled into a recess of the docking cap 402, the biostimulator 100 may be secured for delivery and deployment at the target anatomy. In an embodiment, the biostimulator delivery system applies torque to the biostimulator 100 to screw the anchor 106 of the biostimulator 100 into tissue. Once the anchor 106 is fully inserted into tissue, the tethers can be placed into an un-aligned or "unlocked" configuration, allowing the tethers and distal features 602 to be removed from the attachment feature of the biostimulator 100. Once the tethers are disengaged from the biostimulator 100, the biostimulator delivery system 300 can be removed from the patient, leaving the biostimulator 100 in place at the target tissue site.

Other biostimulator delivery systems may also be employed to deliver a biostimulator 100. Any of these biostimulator delivery systems and associated biostimulators are readily capable of being coupled together in the clinical setting via a loading tool and associated methods discussed below.

Loading Tool

Figure 10A:
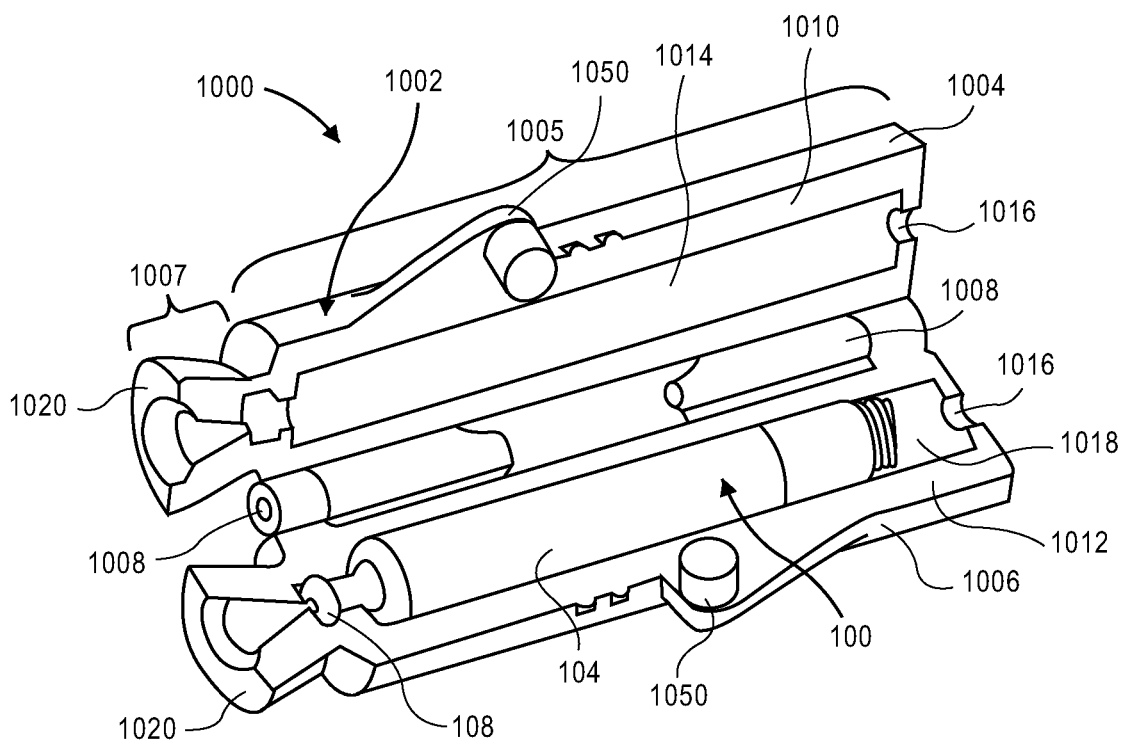
FIGS. 10A-10B are perspective views of a biostimulator system in an open and closed configuration, in accordance with an embodiment.
Figure 10B:
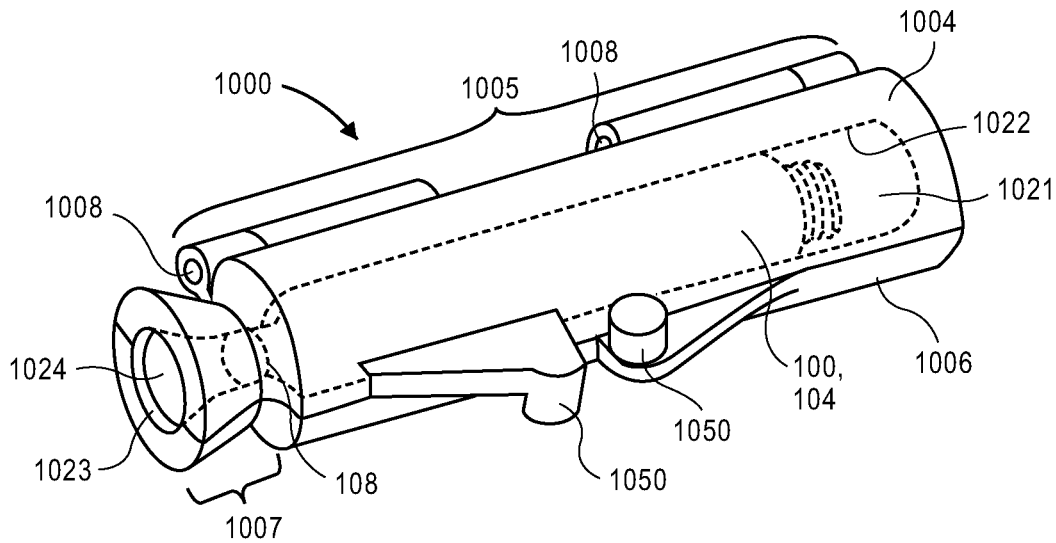

Referring to FIGS. 10A-10B, perspective views of a biostimulator system in an open and closed configuration are shown in accordance with an embodiment. A biostimulator system 1000 includes a loading tool 1002 for loading the biostimulator 100 onto a biostimulator delivery system 300. The biostimulator 100 can be mounted on and/or in the loading tool 1002. For example, the loading tool 1002 can include a first body portion 1004 movably connected to a second body portion 1006, and the biostimulator 100 can be mounted on one of the body portions in an open configuration (FIG. 10A) or mounted in a volume defined by a combination of both body portions in a closed configuration (FIG. 10B). Accordingly, the biostimulator 100 can be packaged or stored in the loading tool 1002.

Referring to FIG. 10A, the loading tool may have a clamshell design to allow the biostimulator to be loaded onto one of the body portions in the open configuration, and then contained by the body portions by closing the body portions against each other. In an embodiment, the second body portion 1006 is hinged to the first body portion 1004. For example, the first body portion 1004 may be pivotally connected to the second body portion 1006 by a hinge 1008. The hinge 1008 can include a pinned connection between hinge elements, or the hinge 1008 may be a living hinge, such as a thin strap of material having ends connected to each of the first body portion 1004 and the second body portion 1006. Accordingly, the hinge 1008 may be integrally formed with the body portions, and the loading tool 1002 may have a monolithic construction.

Each of the body portions may be further segmented, either physically or conceptually, into several subportions. For example, each body portion may have a distal subportion 1005 and a proximal subportion 1007 proximal to the distal subportion 1005. The body portions, and the respective subportions, can include surfaces that mate in the closed configuration. For example, the first body portion 1004 can include a first face 1010, and the second body portion 1006 can include a second face 1012. When the first body portion 1004 is pivoted about the hinge 1008 from the open configuration to the closed configuration, the first face 1010 can appose the second face 1012.

In an embodiment, each body portion includes one or more recesses in the subportions. For example, a first recess 1014 can be formed in the first body portion 1004. The first recess 1014 can project into the first face 1010 and extend from a distal end 1016 of the body portion to a proximal end 1020 of the body portion. Thus, the first recess 1014 can include recess segments in the distal subportion 1005 and the proximal subportion 1007 of the first body portion 1004. Similarly, a second recess 1018 can be formed in the second body portion 1006. The second recess 1018 can project into the second face 1012 and extend from a distal end 1016 of the body portion to a proximal end 1020 of the body portion. Thus, the second recess 1018 can include recess segments in the distal subportion 1005 and the proximal subportion 1007 of the second body portion 1006.

Referring to FIG. 10B, when the first face 1010 is apposed to the second face 1012 in the closed configuration of the loading tool 1002, the first recess 1014 and the second recess 1018 can combine to define a loading volume 1021. In an embodiment, the loading volume 1021 can be further segmented into subvolumes having respective functions. For example, the distal subportion 1005 includes a biostimulator volume 1022 configured to receive the biostimulator 100, and the proximal subportion 1007 includes a catheter volume 1023 configured to receive a portion of the biostimulator delivery system 300, such as the docking cap 402. In an embodiment, the proximal subportion 1007 further includes a funnel having a funnel volume 1024 tapering from the catheter volume 1023 to the biostimulator volume 1022. The distally tapering funnel can guide the tethers into the opening 110 of the docking button 108 to load the biostimulator 100 onto the biostimulator delivery system 300.

The loading volume 1021 and respective subvolumes defined by the internal surfaces of the loading tool body portions may be sized and configured to contain and hold the biostimulator 100. For example, the inner surfaces of the distal subportions 1005 of first body portion 1004 and second body portion 1006, which define the recesses, may be configured to conform to an outer surface of the housing 104 and the docking button 108 of the biostimulator 100. The inner surfaces defining the recesses can be configured to receive the biostimulator 100 and to facilitate joining the biostimulator 100 to the biostimulator delivery system 300.

Figure 11A:
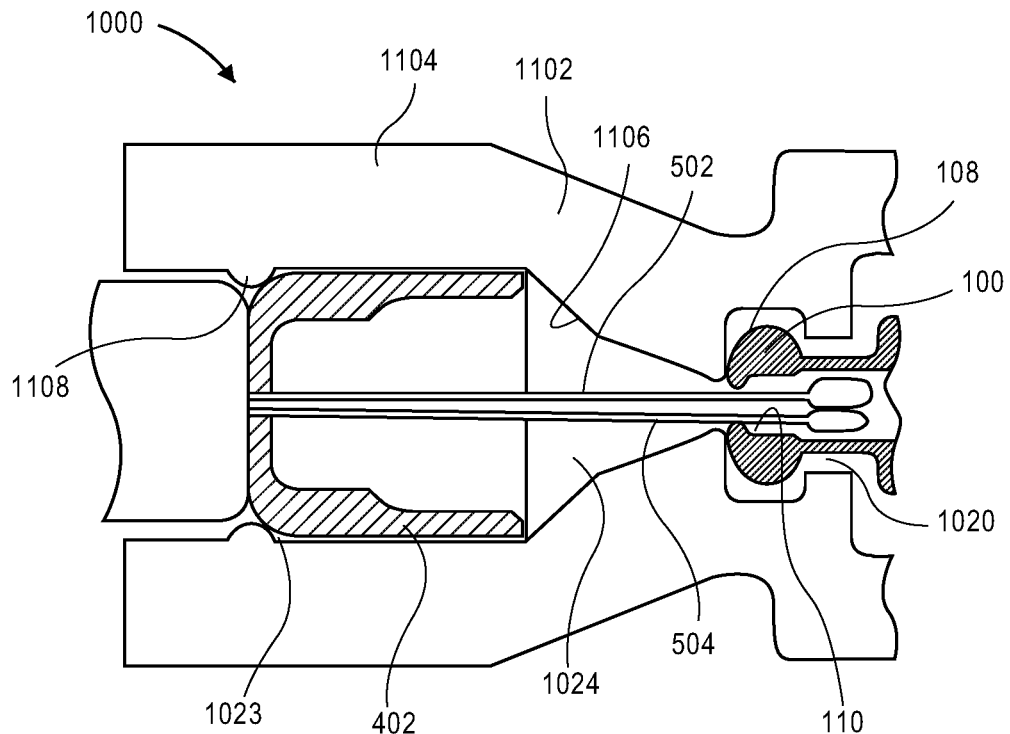
FIGS. 11A-11B are cross-sectional views of a proximal portion of the biostimulator system, in accordance with an embodiment.

Referring to FIG. 11A, a detailed cross-sectional view of a proximal portion of the biostimulator system is shown in accordance with an embodiment. The subportions of the loading tool 1002 in the closed configuration can also be defined as body wall sections. For example, the first body portion 1004 and the second body portion 1006, when apposed to one another, can form a neck 1102. The neck 1102 can be a wall around the funnel volume 1024. An inner surface of the neck 1102 can surround and define the funnel volume 1024 that tapers distally from the catheter volume 1023 used to receive the docking cap 402 to the loading volume 1021 used to receive the biostimulator 100.

The neck 1102 can guide the tethers distally into the biostimulator 100 during the loading process. In an embodiment, a distal opening of the neck 1102, e.g., a distal end of the funnel volume 1024, can have a diameter that is configured to receive one of the distal features 602 of the tethers at a time. As described above, restricting passage of the distal features 602 to a sequential advancement, one after the other, facilitates passage into the opening 110 in the docking button 108 to lock the biostimulator 100 onto the biostimulator delivery system 300. The distally tapering funnel may be a conical, or generally conical, surface that tapers distally. Alternatively, the distally tapering funnel can have other tapering geometries such as, for example, (1) a three, four, or greater-sided pyramidal shape, or (2) a funneling configuration including two opposed converging planes bounded and joined on either side to each other by non-converging or parallel planar sides.

In an embodiment, the loading tool 1002 includes a lead-in feature to guide the tether(s) of the biostimulator system 1000 toward the neck 1102. More particularly, when inserting the tethers of the catheter into a guide barrel 1104, e.g., while advancing the docking cap 402 toward the guide barrel 1104, the tethers can hang on sharp edges within the barrel volume. By way of example, in some embodiments, the inner diameter of the guide barrel volume may be greater than an inner diameter of the funnel volume 1024 at a proximalmost location of the funnel volume 1024. The reduction in diameter may be abrupt, e.g., the transition can be by a transverse ledge extending from the guide barrel 1104 inner surface to the funnel inner surface. In such case, the tethers may catch on the ledge and resist forward motion of the catheter. When the tethers catch on the ledge, a risk of damage to the tethers or the catheter is increased.

To facilitate a smooth insertion of the tethers into the funnel volume 1024 and reduce a likelihood of damage to the tethers and the catheter, the loading tool 1002 can include a taper 1106. The taper 1106 can ease insertion of the tethers. More particularly, the loading tool 1002 can include a tapered surface extending from the guide barrel inner surface to the funnel inner surface. In an embodiment, the tapered surface can make an angle of 40-50 degrees, e.g., 45 degrees, relative to a transverse plane that is orthogonal to a longitudinal axis extending through the guide barrel volume. The tapered ledge can direct the tethers radially inward when the tethers contact the taper 1106. Accordingly, the tethers do not catch on the taper 1106, and a likelihood of damage to the tethers or catheter can be reduced.

The body portions can form other wall sections. In an embodiment, the first body portion 1004 and the second body portion 1006 form a guide barrel 1104. The guide barrel 1104 can be a wall around the catheter volume 1023.

The guide barrel 1104 can extend proximally from the neck 1102 to provide a generally cylindrical port to receive the docking cap 402. More particularly, the docking cap 402 can be inserted into the catheter volume 1023 and an outer surface of the docking cap 402 can face an inner surface of the guide barrel 1104.

The guide barrel 1104 can receive the docking cap 402 in a sliding fit, and thus, the guide barrel 1104 can support the distal end 1016 of the biostimulator delivery system 300 during the loading process. More particularly, the guide barrel 1104 can conform to the docking cap 402 to resist lateral loading on the biostimulator delivery system 300, which could otherwise cause the loading tool 1002 to hang from the catheter end during the loading process, exerting excessive strain on the tethers and potentially leading to kinking of the tethers or the catheter. A likelihood of tether kinking can be reduced by forming, by the guide barrel 1104, a catheter volume 1023 having an axial length that is at least a portion of an axial length of the docking cap 402. In an embodiment, the axial length of the guide barrel 1104 and/or catheter volume 1023 is at least half of the axial length of the docking cap 402. For example, the axial length of the guide barrel 1104 may be at least as long as the axial length of the docking cap 402 that the loading tool 1002 is configured to receive.

In an embodiment, the axial length of the guide barrel 1104 is greater than the axial length of the docking cap 402. A longer guide barrel 1104 not only provides ample support for the docking cap 402 even when the distal end 1016 of the docking cap 402 is not fully inserted into the catheter volume 1023, but also provides additional space for the loading tool 1002 to include engagement features to temporarily lock the biostimulator delivery system 300 to the loading tool 1002.

In an embodiment, the loading tool 1002 includes a detent 1108 extending radially inward from the guide barrel 1104. The detent 1108 can be a ridge extending partially or fully around the central axis passing through the loading volume 1021. More particularly, the ridge can be a circumferential ridge running along the inner surface of the guide barrel 1104 around the catheter volume 1023. Alternatively, the detent 1108 can include one or more bumps extending radially inward such that a distance between an apex of one of the bumps and an inner surface of the guide barrel 1104 circumferentially opposed to the bump is less than a diameter of the catheter volume 1023 that receives the docking cap 402. Accordingly, when the docking cap 402 is positioned in the catheter volume 1023, the detent 1108 is located proximal to the docking cap 402 and engages a rearward facing surface of the docking cap 402. The engagement between the detent 1108 and the docking cap 402 can provide an interference fit between the loading tool 1002 and the docking cap 402 to prevent proximal displacement of the docking cap 402 relative to the neck 1102. Thus, the detent 1108 can temporarily lock the biostimulator delivery system 300 to the loading tool 1002 during the loading process. Such locking features can increase a likelihood that the loading tool 1002 will stay attached to the biostimulator delivery system 300 during the loading process until an operator intentionally opens the loading tool 1002 to release the biostimulator 100 from the loading tool 1002. When the operator opens the loading tool 1002 as described below, the detent 1108 would no longer resist removal of the docking cap 402 from the guide barrel 1104 because the catheter volume 1023 would enlarge as the body portions separate.

Figure 11B:
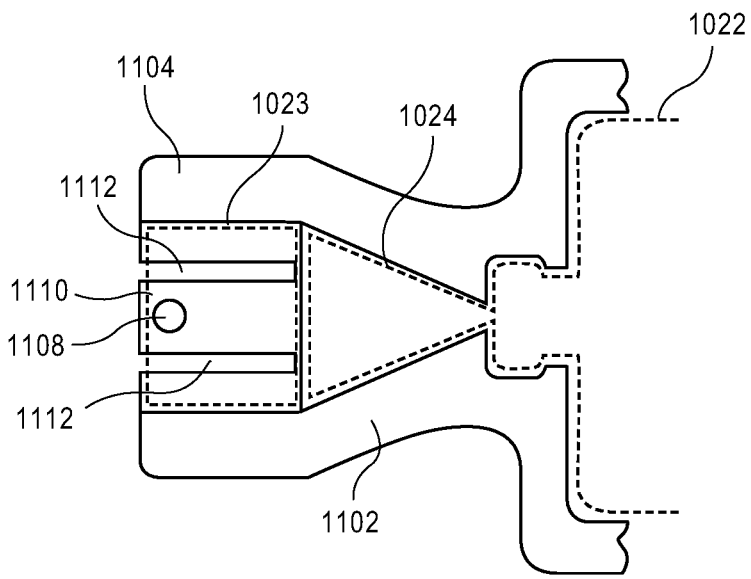

Referring to FIG. 11B, in an embodiment, the guide barrel 1104 can include a spring tab 1110 to resiliently conform to the outer surface of biostimulator delivery system 300. The spring tab 1110 can be formed by one or more slots 1112 extending in an axial direction through the guide barrel 1104. For example, a pair of slots 1112 can extend from a proximal end of the guide barrel 1104 to a distal end of the guide barrel 1104 at the transition into the neck 1102. The pair of slots 1112 can be on each lateral side of the detent 1108. More particularly, the detent 1108 can extend radially inward from the spring tab 1110. Spring tab 1110 can act like a cantilever when an outward force is applied to detent 1108. For example, if an outer surface of docking cap 402 or another portion of biostimulator delivery system 300 presses against detent 1108 when the docking cap 402 is loaded into the catheter volume 1023, the spring tab 1110 can deform outward. The flexibility of the spring tab 1110 can accommodate misalignment of the docking cap 402 without leading to an opening of the proximal portion of the loading tool 1002. For example, when the detent 1108 does not land exactly within the diameter reduction behind the docking cap 402, rather than pushing the first body portion 1004 and the second body portion 1006 apart from each other, the spring tabs 1110 on respective body portions would flex outward without distorting the intended conical geometry of the funnel volume 1024.

As indicated in FIGS. 10A-10B, the first body portion 1004 and the second body portion 1006 may include latching tabs 1050. The latching tabs 1050 can be integrally formed with the body portions 1004, 1006, e.g., formed in a same molding operation as the body portions. The tabs can interface together to secure the first and second body portions 1006 to each other, as shown in FIG. 10B, to enclose the biostimulator 100 in the loading volume 1021. Opening the latching tab embodiment shown in FIGS. 10A-10B may require two-handed operation. For example, an operator may need to use both hands to unlatch the first body portion 1004 from the second body portion 1006. As described below, embodiments of the loading tool 1002 may include a latch to facilitate single-handed opening, i.e., with the use of only one hand, of the loading tool 1002.

Figure 12A:
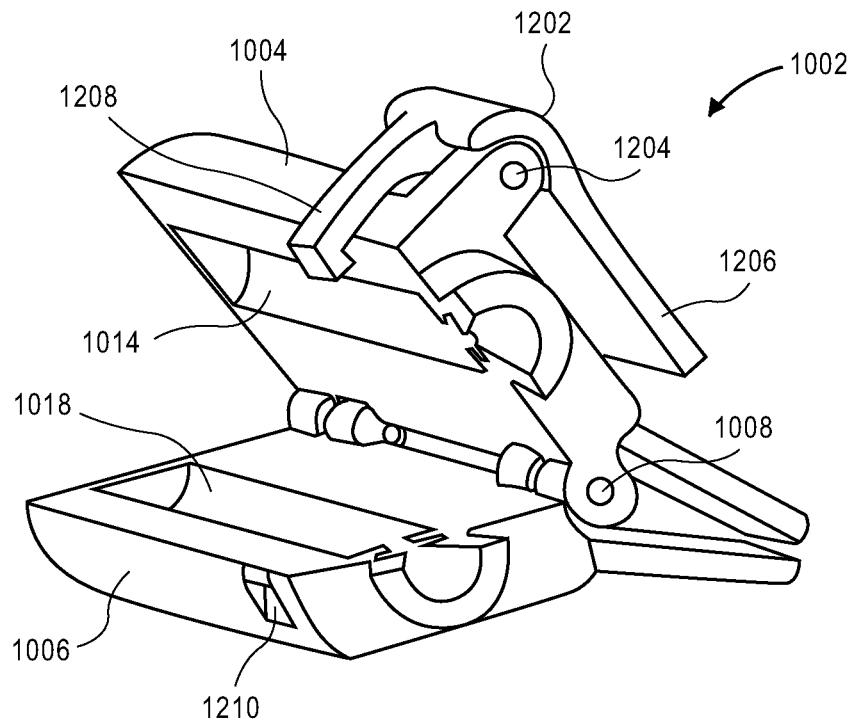
FIGS. 12A-12B are perspective views of a loading tool in an open and closed configuration, and having a hinged latch, in accordance with an embodiment.
Figure 12B:
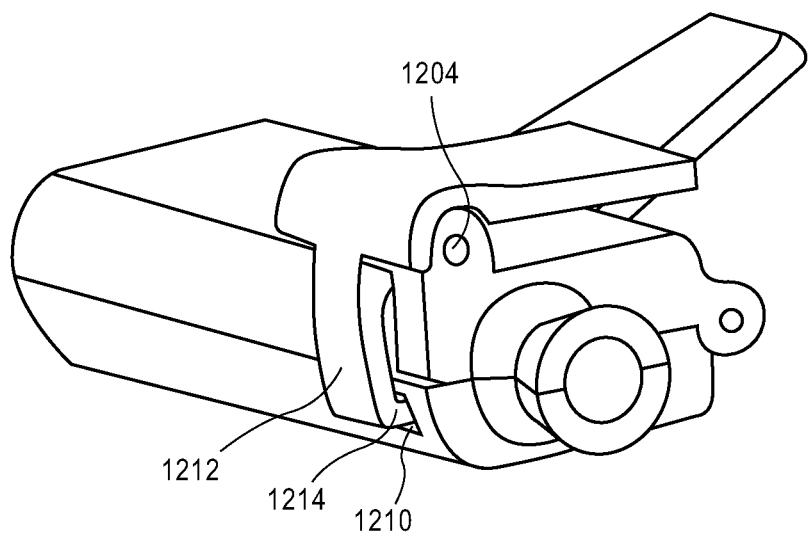

Referring to FIGS. 12A-12B, perspective views of a loading tool in an open and closed configuration, and having a hinged latch are shown in accordance with an embodiment. The loading tool 1002 is described below in relation to illustrations that do not represent the biostimulator 100 in the loading volume 1021, however, it will be appreciated that the biostimulator 100 may be mounted in the loading tool 1002 to form the biostimulator system 1000.

Referring to FIG. 12A, the loading tool 1002 includes the first body portion hinged to the second body portion 1006 by the hinge 1008. In an embodiment, a latch 1202 is mounted on the first body portion 1004. For example, the latch 1202 may be connected to the first body portion 1004 by a latch hinge 1204. The latch hinge 1204 can connect the latch 1202 to the first body portion 1004 in a manner similar to the hinge connection between the first body portion 1004 and the second body portion 1006. For example, the latch hinge 1204 may include a pin to fasten the latch 1202 to the first body portion 1004. Accordingly, the latch 1202 may be hinged to the first body portion 1004 such that a latch tab 1206, which can be a thumb tab extending from the latch hinge 1204, can pivot about the pin relative to the first body portion 1004. The latch 1202 may include a latch hook 1208 extending from the latch tab 1206. The latch hook 1208 can be pivotally connected to the first body portion 1004 by the latch hinge 1204 such that, when an operator presses on the latch tab 1206, the latch hook 1208 pivots and moves relative to the first body portion 1004 and/or the second body portion 1006. The second body portion 1006 can include a keeper 1210 to receive the latch 1202.

Referring to FIG. 12B, the keeper 1210 can be a recess formed in an outer surface of the second body portion 1006. The recess can be sized and positioned such that, when the loading tool 1002 is in the closed configuration and the latch 1202 is in a locked configuration, the latch hook 1208 engages the keeper 1210. More particularly, in the closed configuration, the latch hook 1208 may have a latch shank 1212 extending along the outer surface of the second body portion 1006 from the latch hinge 1204, and a latch tooth 1214 can extend inward from the latch shank 1212 into the recess of the keeper 1210. The latch tooth 1214 can insert into the recess such that, when an opening force is applied to pivot the first body portion 1004 relative to the second body portion 1006, the latch tooth 1214 can interfere with an inner surface of the keeper 1210 to hold the body portions together.

Figure 13A:
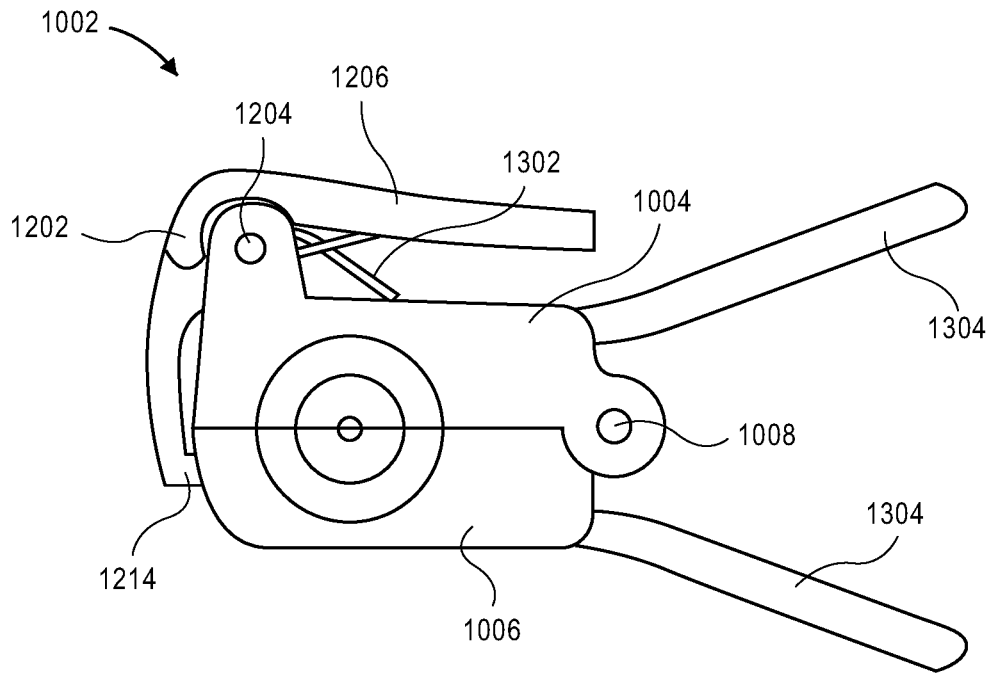
FIGS. 13A-13B are end views of a loading tool having a hinged latch in a locked and unlocked configuration, in accordance with an embodiment.
Figure 13B:
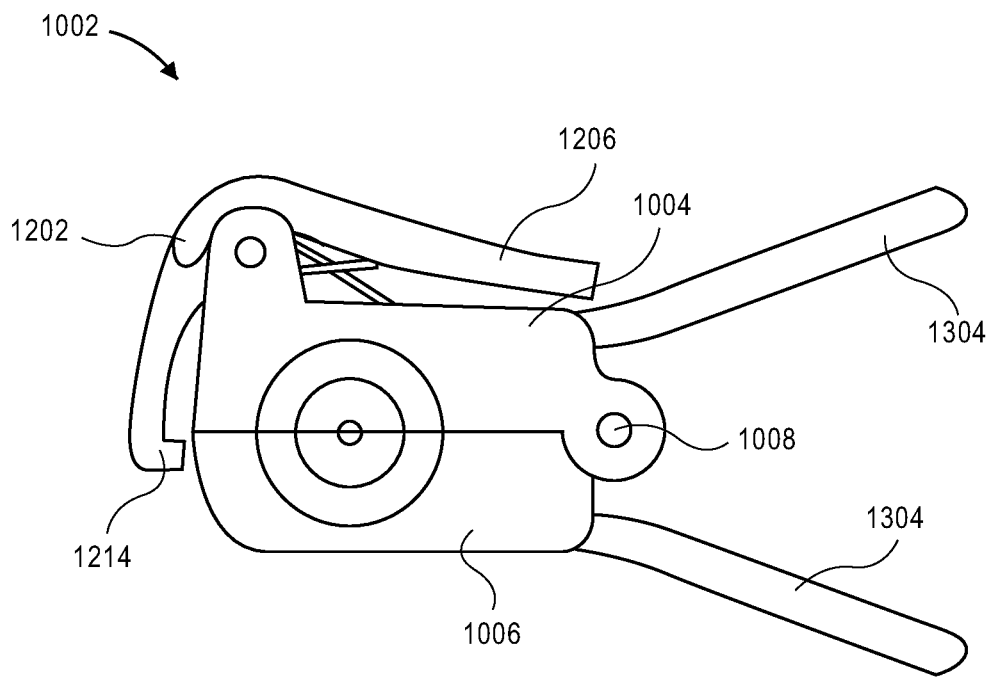

Referring to FIGS. 13A-13B, end views of a loading tool having a hinged latch in a locked and unlocked configuration are shown in accordance with an embodiment. Referring to FIG. 13A, when the loading tool 1002 is in the locked configuration, the latch tooth 1214 extends into the keeper 1210 to resist separation between the first body portion 1004 and the second body portion 1006. In an embodiment, the latch 1202 is spring-loaded to bias the latch 1202 toward either the locked or unlocked configuration. For example, the loading tool 1002 can include a spring 1302 having a first spring end in contact with the latch tab 1206 and a second spring end in contact with the first body portion 1004. The spring 1302 can be secured to the latch hinge 1204. The spring ends act on the latch tab 1206 and the first body portion 1004 to bias the components in a certain direction. For example, the spring 1302 can bias the latch tab 1206 away from the first body portion 1004 to cause the latch tooth 1214 to pivot toward the second body portion 1006.

Referring to FIG. 13B, to unlatch the loading tool 1002, an operator can press on the latch tab 1206. When the latch tab 1206 is pressed with enough force to overcome the bias force of the spring 1302, the latch tooth 1214 can pivot out of the keeper 1210. When the latch tooth 1214 clears the rim of the recess that forms the keeper 1210, the first body portion 1004 and the second body portion 1006 can be separated. For example, after the biostimulator 100 is engaged to the biostimulator delivery system 300, the loading tool 1002 can be unlocked and opened to release the biostimulator 100.

In an embodiment, the loading tool 1002 includes one or more wing tabs 1304 extending outward from the first body portion 1004 and/or the second body portion 1006. The wing tabs 1304 can extend on an opposite side of the hinge 1008 from the body portions. Accordingly, when the wing tabs 1304 are pinched together by a hand of an operator, a torque is generated about the hinge 1008 to separate the body portions when the latch 1202 is not engaged with the keeper 1210.

It will be appreciated that unlatching the latch 1202 and opening the loading tool 1002 can be performed single-handedly. For example, an operator can hold the biostimulator delivery system 300 in a left hand while simultaneously using a right hand to press downward on the latch tab 1206 and squeeze or pinch the wing tabs 1304 together to open the loading tool 1002.

Actuation of the latch tab 1206 and the wing tabs 1304 can be performed as separate operations, or as a singular operation. For example, the latch tab 1206 can also be a wing tab 1304. The latch tab 1206 can extend to the opposite side of the hinge 1008 from the first body portion 1004 and oppose the wing tab 1304 connected to the second body portion 1006 such that pressing on the latch tab 1206 both unlatches the latch 1202 and moves the latch tab 1206 closer to the opposing wing tab 1304. When the wing tabs 1304 are brought together as shown in FIG. 12A, each of the biostimulator delivery system 300 and the biostimulator 100 can be removed from the loading tool 1002. The operator can use the right hand to remove the loading tool 1002 from the biostimulator delivery system 300 that is held in the left hand, and thus, unlocking the latch 1202 and removal of the loading tool 1002 can be performed single-handedly. The biostimulator 100 can then be moved from the undocked configuration to the docked configuration (FIGS. 8-9) for delivery to the target anatomy.

Figure 14A:
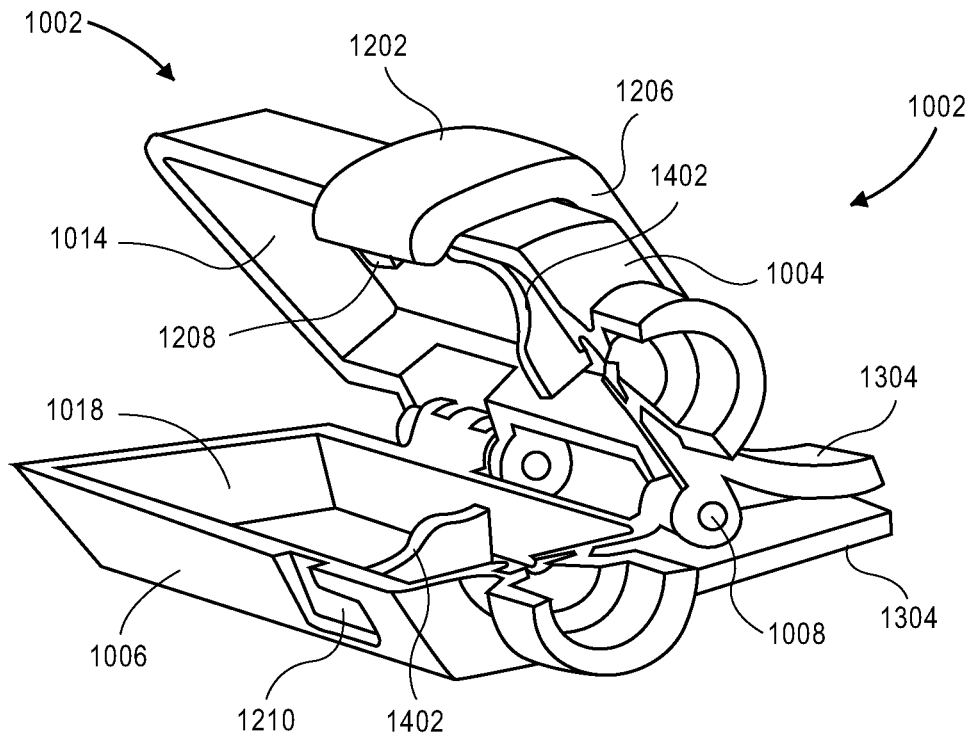
FIGS. 14A-14B are perspective views of a loading tool in an open and closed configuration, and having a sliding latch, in accordance with an embodiment.
Figure 14B:
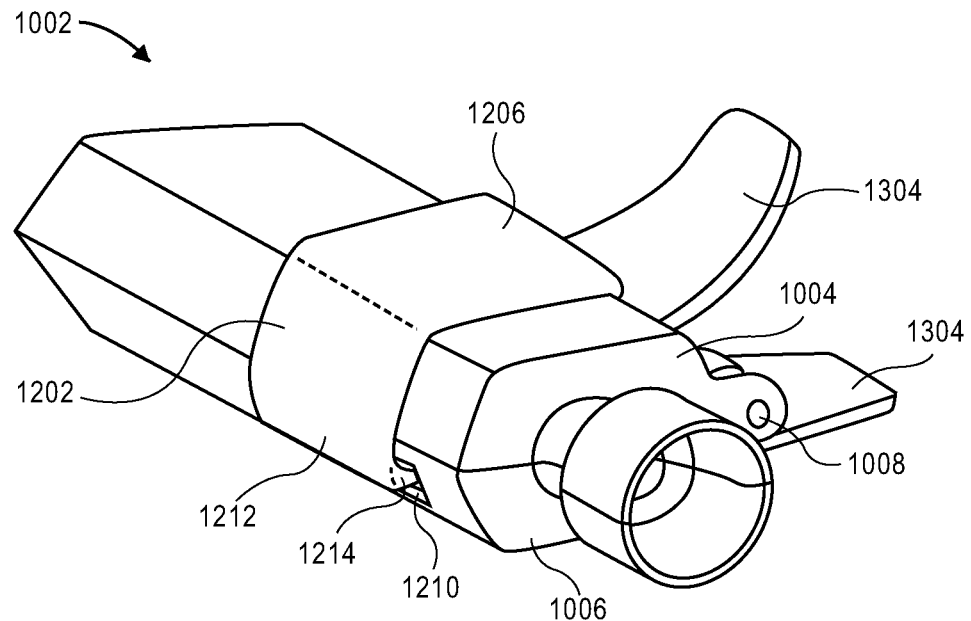

Referring to FIGS. 14A-14B, perspective views of a loading tool in an open and closed configuration, and having a sliding latch are shown in accordance with an embodiment. Referring to FIG. 14A, the latch 1202 may be slidably mounted on the first body portion 1004. By way of example, the latch tab 1206 may have a prong that inserts into a slot of the first body portion 1004 (not shown). The prong can be retained in the slot, e.g., with a clip, such that the latch tab 1206 is retained on the first body portion 1004 and able to slide over the first body portion 1004 based on a camming action of the prong in the slot. More particularly, the first body portion 1004 and the latch tab 1206 can be connected by a prismatic joint that allows the latch tab 1206 a degree of freedom in the axial direction relative to the first body portion 1004. For example, in an embodiment, the slot in the first body portion 1004 is axially arranged, and thus, the latch tab 1206 can slide over the first body portion 1004 in a proximal and distal direction. Accordingly, the latch hook 1208 can extend from the latch tab 1206 and be movable axially along a side surface of the first body portion 1004 and/or the second body portion 1006. When an operator slides the latch tab 1206 distally, the latch hook 1208 can move distally, and when the operator slides the latch 1202 proximally, the latch hook 1208 can move proximally. The second body portion 1006 can include a keeper 1210 to receive the latch 1202.

In an embodiment, the space formed by the combined first recess 1014 and second recess 1018 can be substantially larger than a volume of the biostimulator 100 that is contained within the loading tool 1002. For example, the first body portion 1004 can have a shell structure that includes a thin wall, and thus, the inner surface of the first body portion 1004 that partly defines the first recess 1014 can be approximately the same size as the outer surface of the first body portion 1004. To constrain movement of the biostimulator 100 within the loading tool 1002, one or more rests 1402 can be included within the loading tool recesses. For example, the first recess 1014 and second recess 1018 can contain respective rests 1402. The rests 1402 can be thin walls projecting inward from the inner surface of the body portions. The rests 1402 can have planar faces that extend orthogonal to a central axis of the loading tool 1002. In an embodiment, the rests 1402 are axially aligned, and include respective curves in their inward surfaces, e.g., half-circle arcs, that face each other. The half-circle arcs can, for example, form a circular opening in the walls of the rests 1402 when the loading tool 1002 is in a closed configuration. In an embodiment, the circular opening receive the biostimulator 1002 and holds the housing 104 in place when the biostimulator 100 is contained within the loading tool 1002.

Referring to FIG. 14B, the keeper 1210 can be a recess formed in an outer surface of the second body portion 1006.

The recess can be sized and positioned such that, when the loading tool 1002 is in the closed configuration and the latch 1202 is in a locked configuration, the latch hook 1208 engages the keeper 1210. More particularly, the latch hook 1208 may have a latch shank 1212 extending along the outer surface of the second body portion 1006 from the latch tab 1206, and a latch tooth 1214 can extend inward from the latch shank 1212. The latch tooth 1214 can extend into the recess of the keeper 1210 such that, in the locked configuration, the latch tooth 1214 can interfere with an inner surface of the keeper 1210 to hold the body portions together.

In an embodiment, one or more of the wing tabs 1304 have a curved profile. For example, the wing tab 1304 extending from the first body portion 1004 in FIG. 14B can have an upward curvature as it extends outward from the first body portion 1004. This curvature can be contrasted with the profile of the wing tab 1304 that extends outward from the second body portion 1006 in FIG. 14B. More particularly, the wing tab 1304 can extend along a flat plane from the second body portion. Accordingly, a distance between the wing tabs 1304 can increase in the outward direction, e.g. the distance near the hinge 1008 can be less than the distance at the outward tips of the wing tabs 1304. The curvature of one or more wing tab 1304 can provide an ergonomic, e.g., comfortable, grip of the wing tabs 1304. Furthermore, the curvature separates the tips of the wing tabs 1304, allowing the user to open the body portions to a greater degree before the wing tabs 1304 contact each other and prevent further opening.

Figure 15A:
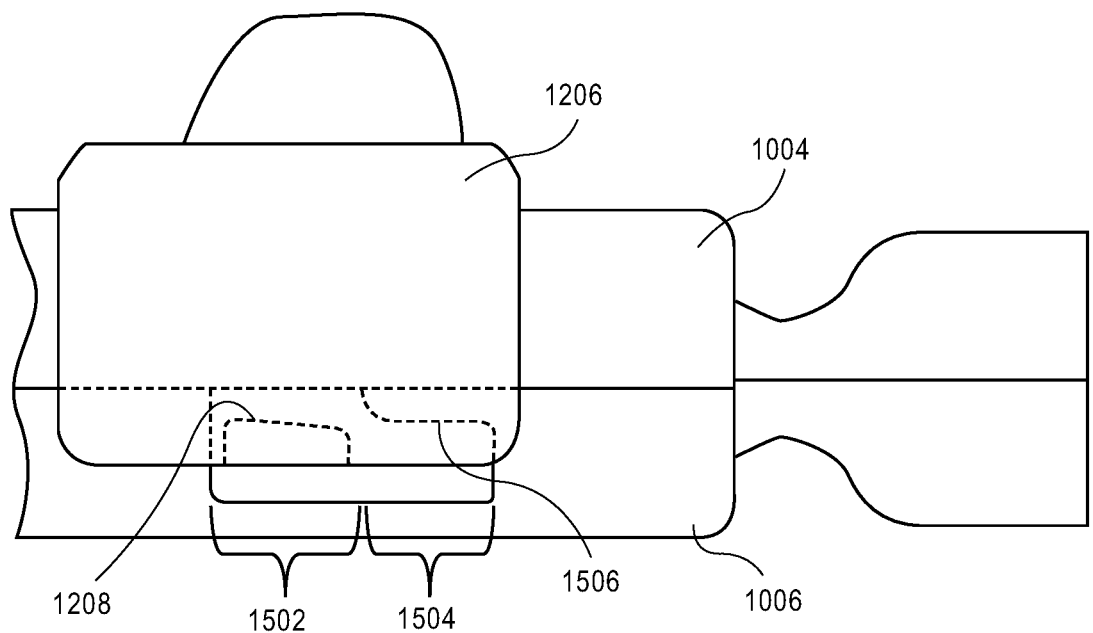
FIGS. 15A-15B are side views of a loading tool having a sliding latch in a locked and unlocked configuration, in accordance with an embodiment.
Figure 15B:
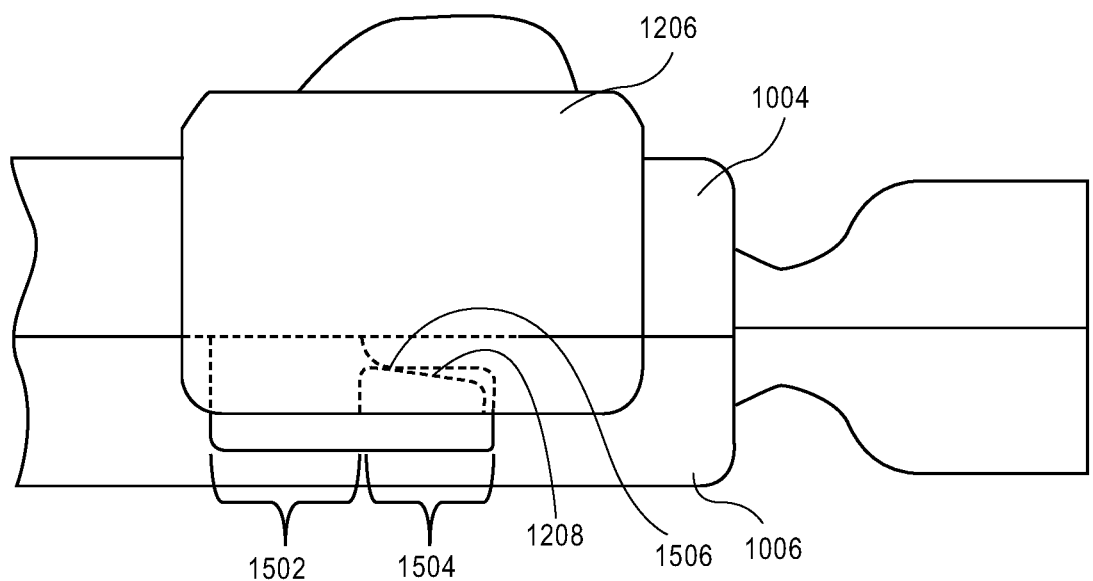

Referring to FIGS. 15A-15B, side views of a loading tool having a sliding latch in a locked and unlocked configuration are shown in accordance with an embodiment. Referring to FIG. 15A, when the loading tool 1002 is in the unlocked configuration, the latch tooth 1214 extends into a portion of the keeper 1210 that does not have an upper edge to resist upward movement of the latch tooth 1214. For example, the keeper recess can have a generally L-shaped profile having a vertical section 1502 and a horizontal section 1504. The vertical section 1502 can allow the latch hook 1208 to move freely upward and downward, and thus, allow the first body portion 1004 and the second body portion 1006 to pivot freely about the hinge 1008. By contrast, the horizontal section 1504 can include an upper ledge 1506 that is vertically above the latch tooth 1214 when the latch hook 1208 is moved into the horizontal section 1504.

Figure 16A:
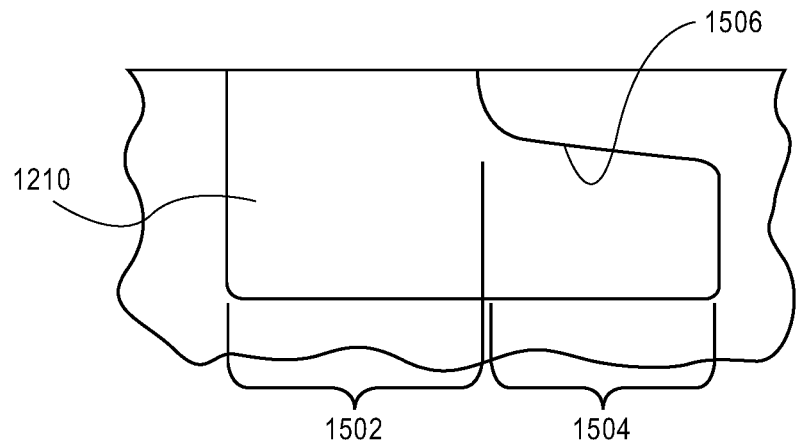
FIGS. 16A-16B are various views of a keeper having a tapered ledge, in accordance with an embodiment.
Figure 16B:
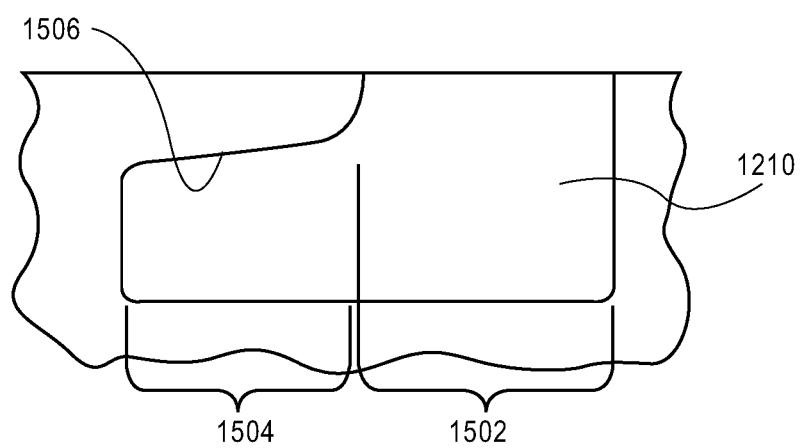

Referring to FIG. 15B, the latch hook 1208 can be moved into the horizontal section 1504 of the keeper 1210 by sliding the latch tab 1206 relative to the first body portion 1004. The horizontal section 1504 can be distal to the vertical section 1502, or proximal to the vertical section 1502 (FIGS. 16A-16B). Accordingly, the latch 1202 can be considered to be a slide-forward-to-lock latch 1202, or a slide-backward-to-lock latch, in various embodiments. When the latch hook 1208 is in the horizontal section 1504, the latch tooth 1214 can be below the ledge 1506, and thus, the keeper 1210 can resist upward movement of the latch tab 1206. More particularly, the latch hook 1208 can lock the first body portion 1004 against the second body portion 1006.

Referring to FIGS. 16A-16B, various views of a keeper having a tapered ledge are shown in accordance with an embodiment. Referring to FIG. 16A, the keeper 1210 is an example of a keeper for a slide-forward-to-lock latch 1202 because the horizontal section 1504 is distal to the vertical section 1502. In an embodiment, the ledge 1506 of the keeper 1210 can taper in a vertical direction. For example, an end of the ledge 1506 where the horizontal section 1504 meets the vertical section 1502 can be vertically higher than the ledge 1506 at an opposite end of the horizontal section 1504. The ledge 1506 therefore forms a ramp over which the latch tooth 1214 slides when the latch tab 1206 is moved from the unlocked configuration to the locked configuration. As the latch tooth 1214 slides, the ramped ledge 1506 can force the latch hook 1208 downward and pull the first body portion 1004 against the second body portion 1006. This wedging action can both secure the body portions more tightly, and can provide a resistive force that reduces a likelihood of accidentally unlatching the latch 1202.

Referring to FIG. 16B, the keeper 1210 is an example of a keeper for a slide-backward-to-lock latch 1202 because the horizontal section 1504 is proximal to the vertical section 1502. In an embodiment, the ledge 1506 of the keeper 1210 can taper in a vertical direction. For example, an end of the ledge 1506 where the horizontal section 1504 meets the vertical section 1502 can be vertically higher than the ledge 1506 at an opposite end of the horizontal section 1504. The ledge 1506 therefore forms a ramp over which the latch tooth 1214 slides when the latch tab 1206 is moved from the unlocked configuration to the locked configuration. As the latch tooth 1214 slides, the ramped ledge 1506 can force the latch hook 1208 downward and pull the first body portion 1004 against the second body portion 1006. This wedging action can both secure the body portions more tightly, and can provide a resistive force that reduces a likelihood of accidentally unlatching the latch 1202.

Figure 17A:
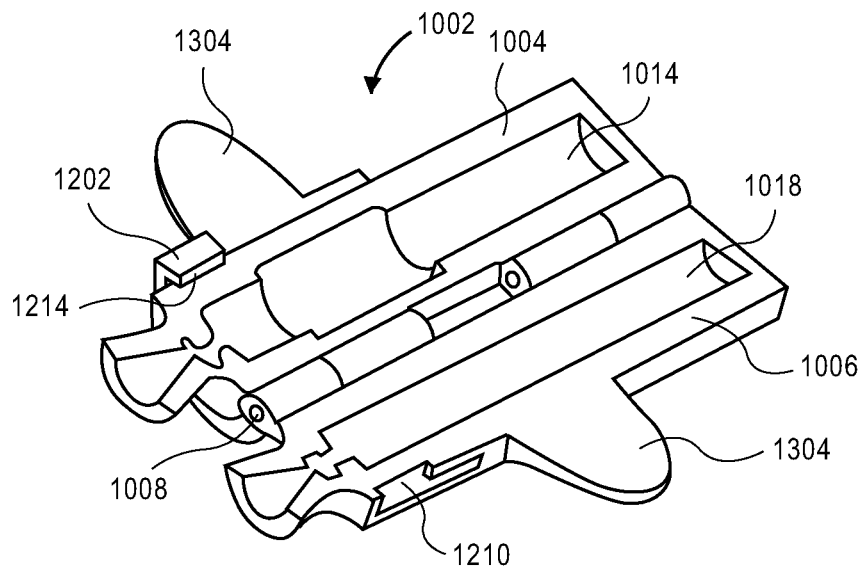
FIGS. 17A-17C are various views of a loading tool having a slide latch including wing tabs, in accordance with an embodiment.
Figure 17B:
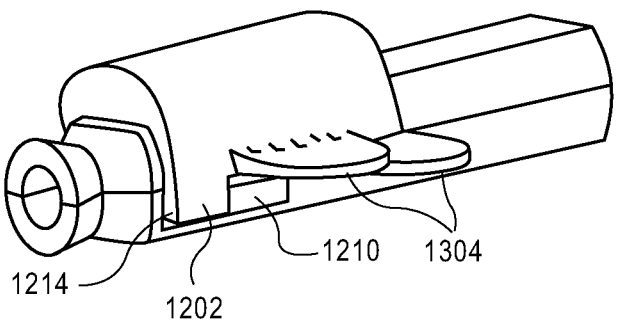
Figure 17C:
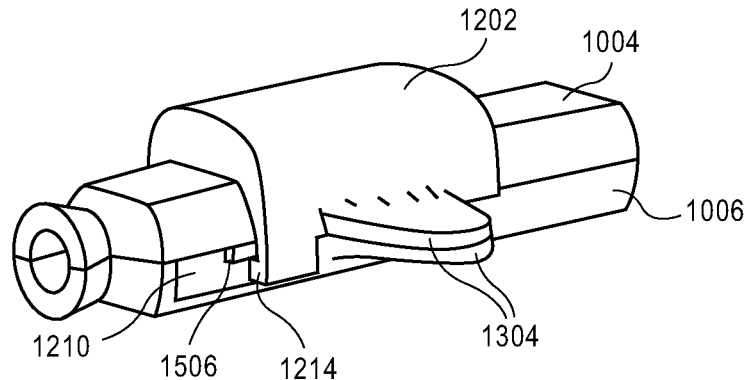

Referring to FIGS. 17A-17C, various views of a loading tool having a slide latch including wing tabs are shown in accordance with an embodiment. Referring to FIG. 17A, in an open state, the loading tool 1002 includes the first body portion 1004 hinged to the second body portion 1006 such that the first recess 1014 and the second recess 1018 are exposed to receive the biostimulator 100. One or more of the body portions can include a wing tab 1304 on the same side of the hinge 1008 as the latch 1202. For example, a wing tab 1304 can extend from the second body portion 1006, and a wing tab 1304 can also extend from the latch 1202 that is mounted on the first body portion 1004.

Referring to FIG. 17B, in a closed state, the wing tabs 1304 can be on the same side of the hinge 1008 as the latch 1202. The latch tooth 1214 can move downward into the vertical section 1502 of the keeper 1210 when the first body portion 1004 is pivoted against the second body portion 1006. Accordingly, the loading tool 1002 can be in a closed and unlocked state.

Referring to FIG. 17C, the slide latch can be slid distally over the first body portion 1004 to align the wing tabs 1304. More particularly, the wing tab 1304 projecting from the slide latch can be vertically above the wing tab 1304 projecting from the second body portion 1006. When the wing tabs 1304 are aligned, the latch tooth 1214 can be below the ledge 1506 and within the horizontal section 1504 of the keeper 1210. Accordingly, the loading tool 1002 can be in a closed and locked state.

It will be appreciated that the embodiment illustrated in FIGS. 17A-17C is an example of a loading tool 1002 that allows an operator to single-handedly lock/unlock the latch 1202 and open/close the loading tool 1002. Rather than open the loading tool 1002 using a pinching action, however, the operator can flip the wing tabs 1304 apart when the latch 1202 is unlocked to cause the body portions to separate.

Figure 18A:
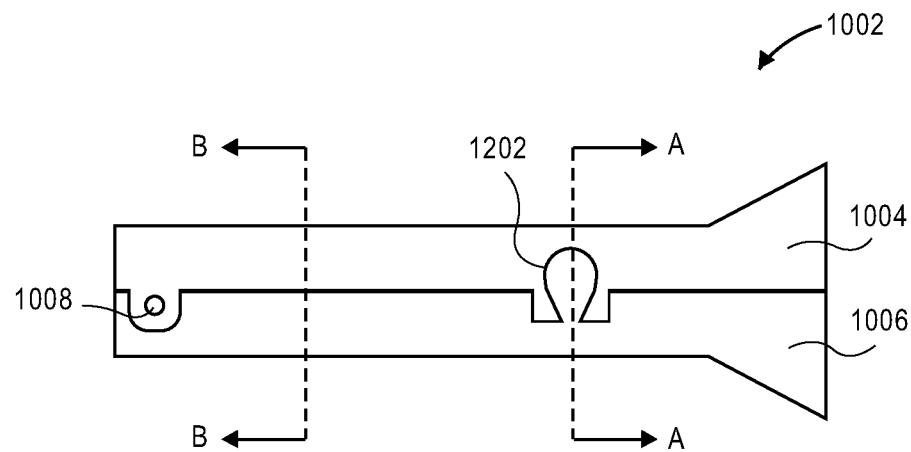
FIGS. 18A-18E are various views of a loading tool having spring-loaded body portions, in accordance with an embodiment.

Referring to FIGS. 18A-18D, various views of a loading tool having spring-loaded body portions are shown in accordance with an embodiment. The loading tool 1002 can be configured to open automatically when unlatched. Referring to FIG. 18A, the first body portion 1004 can be hinged to the second body portion 1006 by the hinge 1008. In an embodiment, the hinge 1008 is located near a distal end of the loading tool 1002, and includes a pivot axis that extends orthogonal to the central axis of the loading tool 1002. Accordingly, rather than pivoting about a lateral edge, the first body portion 1004 pivots about a distal edge. The loading tool 1002 can be packaged with the first body portion 1004 and the second body portion 1006 held together by the latch 1202. As described above, the biostimulator 100 may be contained within the loading volume 1021 of the loading tool 1002. The funnel of the loading tool 1002 can be at the proximal end of the loading tool 1002, opposite of the hinge 1008.

Figure 18B:
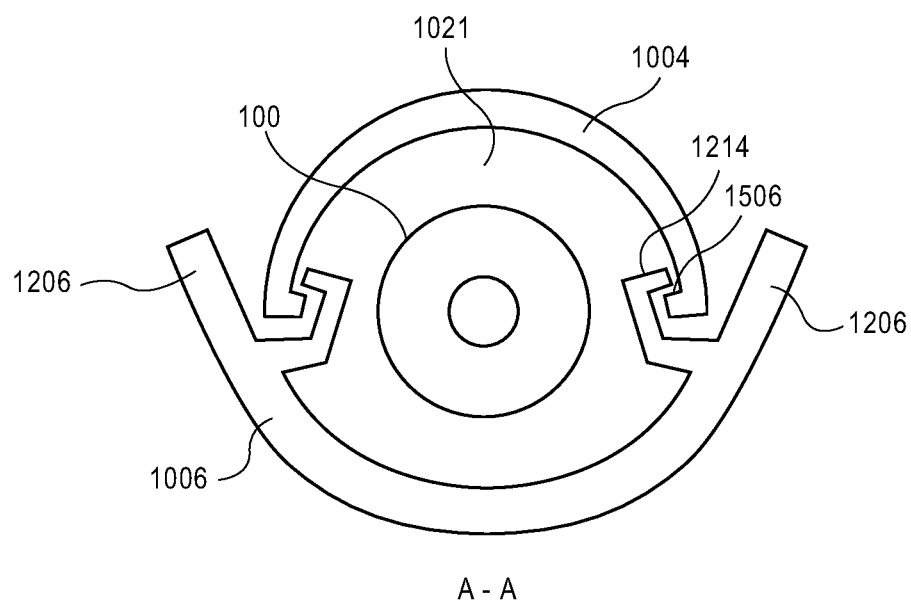

Referring to FIG. 18B, a cross-sectional view taken about line A-A of FIG. 18A is shown. In embodiment, the latch 1202 can be mounted on the second body portion 1006. The latch 1202 may include one or more latch tabs 1206 located on opposite sides of the body portions. The first body portion 1004 can include the keeper, which may be configured as a ledge 1506 extending radially inward from an inner wall of the body portion. Each latch tab 1206 can be associated with a latch tooth 1214 that engages the ledge 1506 of the keeper 1210 in the locked configuration.

The latch 1202 of the loading tool 1002 can be unlocked by squeezing the latch tab(s) radially inward. For example, an operator can pinch the latch tabs 1206 together to bias the latch teeth inward. When the latch teeth 1214 clear the inner edge of the ledge 1506, the first body portion 1004 can be free to move upward relative to the second body portion 1006. More particularly, the first body portion 1004 can pivot about the hinge 1008 to separate from the second body portion 1006 to open the loading volume 1021.

Figure 18C:
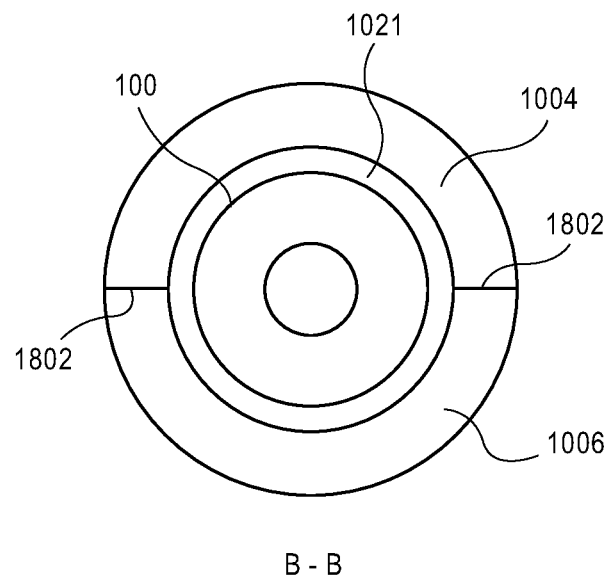

Referring to FIG. 18C, a cross-sectional view taken about line B-B of FIG. 18A is shown. The first body portion 1004 and the second body portion 1006 can each have walls with semi-circular profiles. The semicircular profiles can meet along seams 1802 that are diametrically opposed on opposite sides of the biostimulator 100. Accordingly, the first body portion 1004 and the second body portion 1006 can combine to form a generally cylindrical wall having a loading volume 1021 to receive the biostimulator 100.

Figure 18D:
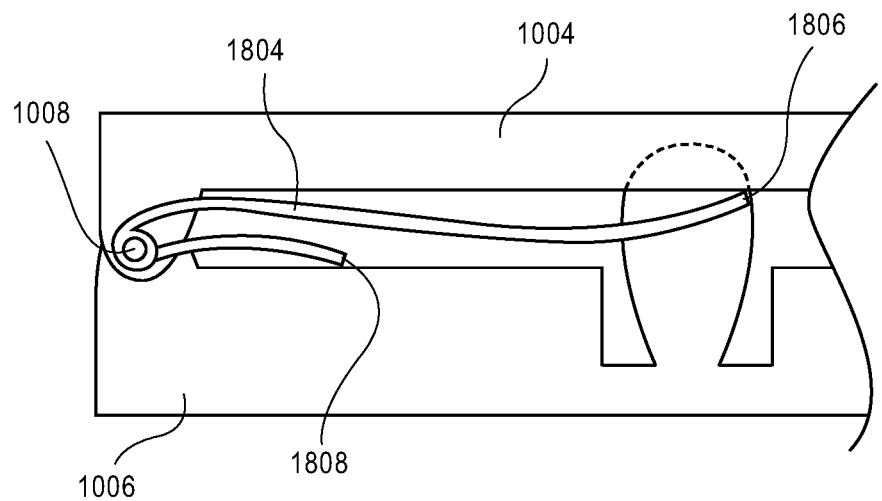

Referring to FIG. 18D, the loading tool 1002 can include a spring 1804 to bias the first body portion 1004 toward or away from the second body portion 1006. For example, the spring 1804 may have a first end 1806 acting on the first body portion 1004 and a second end 1808 acting on the second body portion 1006. The spring 1804 can be connected to one or both of the body portions. In an embodiment, when the latch 1202 is unlocked, the spring 1804 can force the first body portion 1004 away from the second body portion 1006. The first body portion 1004 can pivot about the hinge 1008, and open the loading volume 1021 to expose the biostimulator 100. As described above, the loading tool 1002 can be opened after the tethers are engaged with the docking button 108. Accordingly, to remove the loading tool 1002, the operator can squeeze the latch 1202 to pop the body portions apart, and then remove the loading tool 1002 from the biostimulator 100 that is connected to the biostimulator delivery system 300.

Figure 18E:
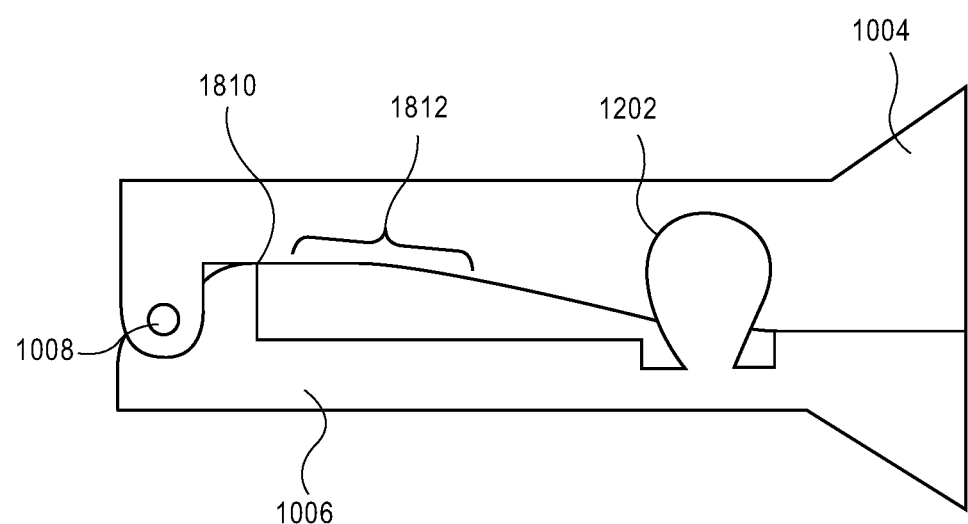

Referring to FIG. 18E, the spring-loaded body portions may be forced away from each other by internal resilience of the body portions themselves, rather than by an additional spring component. In other words, the spring that biases the first body portion 1004 toward or away from the second body portion 1006 may be integral to one or both of the body portions.

In an embodiment, the first body portion 1004 is connected to the second body portion 1006 at the hinge 1008 to pivot relative to the second body portion 1006 about a distal end of the loading tool 1002. When the first body portion 1004 is brought toward the second body portion 1006, e.g., rotated in a clockwise direction in the illustration, an inner surface of the first body portion 1004 can contact a fulcrum 1810 of the second body portion 1006. The fulcrum 1810 can be a pivot point about which a region of the first body portion 1004 extending proximally from the fulcrum 1810 can be cantilevered. More particularly, when the first body portion 1004 contacts the fulcrum 1810 and is forced further downward, a bending moment is applied to the first body portion 1004 about the fulcrum 1810. The bending moment can cause a deformation region 1812 to develop within the first body portion 1004, and the first body portion 1004 can bend toward the second body portion 1006. When the first body portion 1004 bends, the latch tooth 1214 on one body portion can engage the ledge 1506 on the other body portion and the body portions can lock together. In the locked configuration, the deformation region 1812 may remain under stress.

When under stress, the deformation region 1812 is a region of strain. In an embodiment, the strain is elastic strain. That is, the strain may not be above the elastic limit of the material forming the first body portion 1004. In an embodiment, after loading the biostimulator 100 onto the biostimulator delivery system 300, the latch 1202 can be actuated to release the latch tooth 1214 from the ledge 1506. Accordingly, the downward force on the first body portion 1004 can be released. When the first body portion 1004 becomes unconstrained, the deformation region 1812 can resiliently return to the unstrained configuration. The resilience acts as an integral spring within the first body portion 1004 to bias the first body portion 1004 away from the second body portion 1006. The loading tool 1002 can then be removed from the biostimulator 100 and the biostimulator delivery system 300.

Figure 19A:
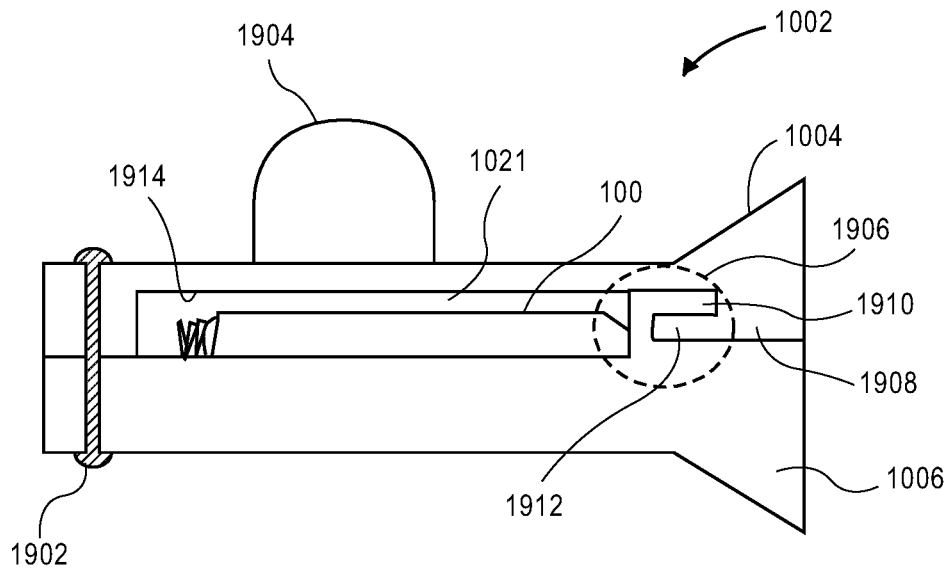
FIGS. 19A-19D are various views of a loading tool having pivoting body portions, in accordance with an embodiment.

Referring to FIGS. 19A-19D, various views of a loading tool having pivoting body portions are shown in accordance with an embodiment. The loading tool 1002 can be configured to open in a side pivoting action. Referring to FIG. 19A, the first body portion 1004 can be hinged to the second body portion 1006 by a hinge pin 1902. In an embodiment, the hinge pin 1902 is located near a distal end of the loading tool 1002, and includes a pivot axis that extends vertically, e.g., along a vertical plane, and orthogonally to the central axis of the loading tool 1002. Accordingly, rather than pivoting about the distal edge and separating within the vertical plane, the first body portion 1004 and the second body portion 1006 can pivot and swing relative to each other in a transverse plane extending into the page. The biostimulator 100 may be contained within the loading volume 1021 of the loading tool 1002. The funnel of the loading tool 1002 can be at the proximal end of the loading tool 1002, opposite of the hinge pin 1902.

Transverse movement of the body portions about the pivot point formed by the hinge pin 1902 can be facilitated by a tab 1904 extending outward from one or more of the body portions. For example, the tab 1904 may be a thumb push tab 1904 extending upward from the first body portion 1004. The tab 1904 has a surface upon which the user can press while steadying the second body portion 1006 and/or the catheter such that a separation force is applied between the first body portion 1004 and the second body portion 1006. The separation force can urge the first body portion 1004 away from the second body portion 1006 within the transverse plane from the closed configuration (FIG. 19A) to the open configuration (FIG. 19B).

In the closed configuration, the first body portion 1004 can be interlocked with the second body portion 1006. In an embodiment, the loading tool 1002 includes an interlocking clasp 1906 closure to join the body portions. The closure can include clasps, e.g., a top clasp 1908 or a bottom clasp 1910, on either or both of the body portions. The clasps can have respective clasp lips that can slide over each other in the transverse direction. In the interlocked position, the clasp lips prevent vertical movement of the body portions. More particularly, an upper surface of the top clasp lip 1912 can engage a lower surface of the bottom clasp 1910 to resist separation in the vertical direction. The clasp lips can be "L" or hook-shaped. The clasp lips may have ramp features that deflect and snap into a desired position. The upper and lower surfaces can hook each other to resist vertical movement, however, the surfaces may slide over each other to allow the body portions to move from the closed configuration to the open configuration laterally.

In an embodiment, the first body portion 1004 includes an open sidewall 1914 on at least one side of the biostimulator 100 in the closed configuration. The open sidewall 1914 can allow the moving body portion to open by sliding over and clearing the biostimulator 100. More particularly, a bottom surface of a distal portion of the first body portion 1004 can be vertically below a highest point on the biostimulator 100, and thus, the open sidewall 1914 can be shaped such that an upper edge of the open sidewall 1914 is vertically above the highest point on the biostimulator 100. The first body portion 1004 can then swing about the hinge pin 1902 without the upper edge of the open sidewall 1914 contacting the biostimulator 100.

Figure 19B:
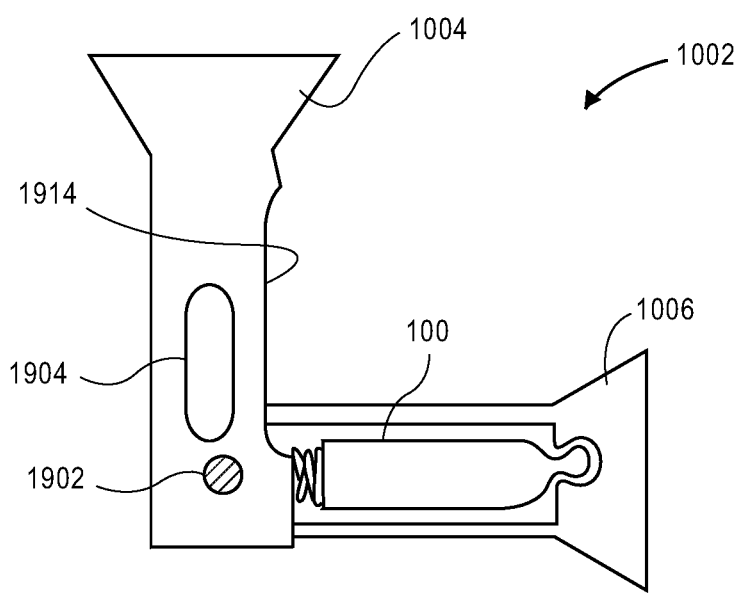

Referring to FIG. 19B, the loading tool 1002 is shown in the open configuration. When the user presses on the tab 1904, the first body portion 1004 rotates about the hinge pin 1902 to cause a lateral angle between the first body portion 1004 and the second body portion 1006 to increase. More particularly, a longitudinal axis extending along the first body portion 1004 separates in a transverse direction from the central axis extending through the biostimulator 100, which is held within the second body portion 1006. The lateral angle within the transverse plane and between the axes increases. In the open configuration, the loading tool 1002 can be removed from the biostimulator 100 and the catheter (not shown).

Figure 19C:
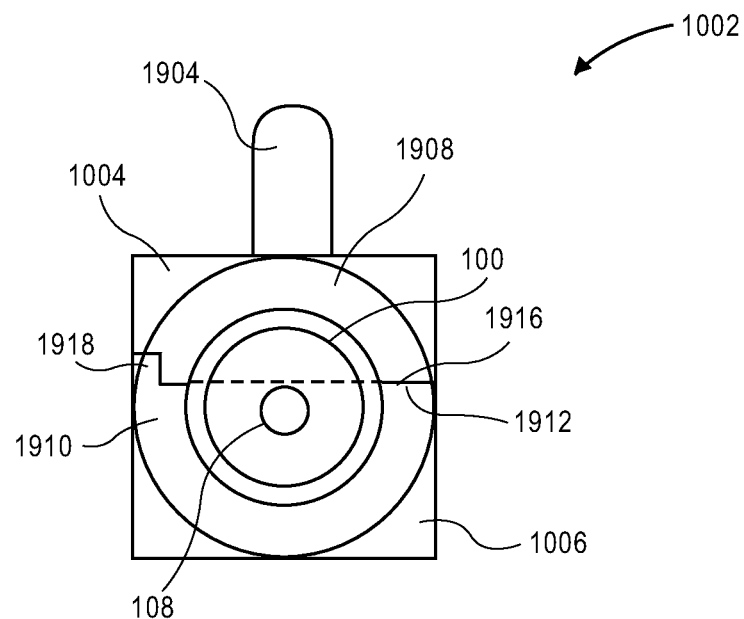

Referring to FIG. 19C, the loading tool 1002 can include additional features to allow the first body portion 1004 to clear the biostimulator 100 when the user opens the tool. For example, similar to the open sidewall 1914, which allows the first body portion 1004 to clear the housing 104 of the biostimulator 100, a proximal portion of the loading tool 1002 may be configured to clear the docking button 108 of the biostimulator 100 when the tool is opened. In an embodiment, the top clasp lip 1912 has a clearance surface 1916 extending along a transverse plane. For example, the clearance surface 1916 can be a surface of the top clasp lip 1912 that is a lower surface of the lip as shown in FIG. 19A. In an embodiment, the clearance surface 1916 of the top clasp lip 1912 is vertically above a highest point on the docking button 108. For example, the dashed line indicating the transverse plane along which the clearance surface 1916 extends is above the highest point on the docking button 108. When the user presses on the tab 1904 to pivot the first body portion 1004 relative to the second body portion 1006 about the hinge pin 1902 (FIG. 19B), the clearance surface 1916 will move along the transverse plane 1922 above the docking button 108. Accordingly, the top clasp lip 1912 will clear the docking button 108 to allow the first body portion 1004 to open.

In an embodiment, a stop 1918 feature is incorporated in one or more of the body portions to provide a unidirectional side pivoting action. For example, the stop 1918 can be a ledge extending upward from the bottom clasp 1910. When the loading tool 1002 is in the closed configuration, the top clasp 1908 can be urged against the stop 1918, however, the top clasp 1908 may not move beyond the stop 1918. A locking feature, such as a detent, may be incorporated in the interlocking clasp closure to maintain the top clasp 1908 against the stop 1918. The user can press on the tab 1904 to urge the top clasp 1908 away from the stop 1918, and to open the loading tool 1002.

Figure 19D:
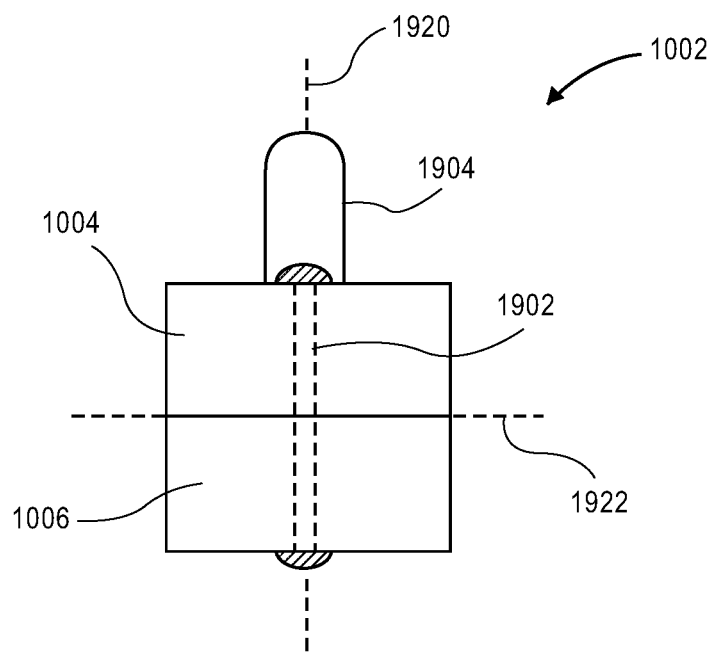

Referring to FIG. 19D, reference geometry is provided to assist in understanding the description above. The vertical plane 1920 can intersect the transverse plane 1922 at the central axis of the biostimulator 100. The tab 1904 and the hinge pin 1902 may extend vertically along the vertical plane 1920 and orthogonal to the transverse plane 1922. By contrast, the surfaces of the first body portion 1004 and the second body portion 1006 that slide over each other during the opening and closing of the loading tool 1002 can extend parallel to each other in a direction of the transverse plane 1922.

Figure 20A:
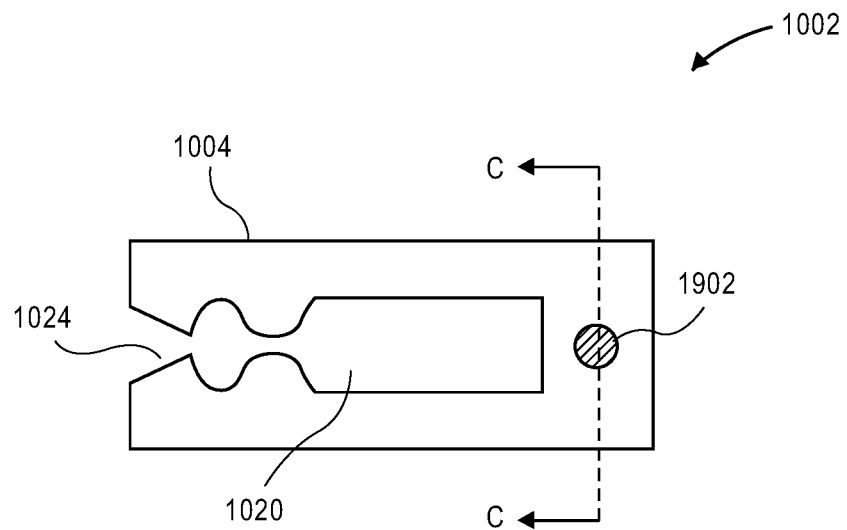
FIGS. 20A-20B are various views of a loading tool having spring-loaded pivoting body portions, in accordance with an embodiment.
Figure 20B:
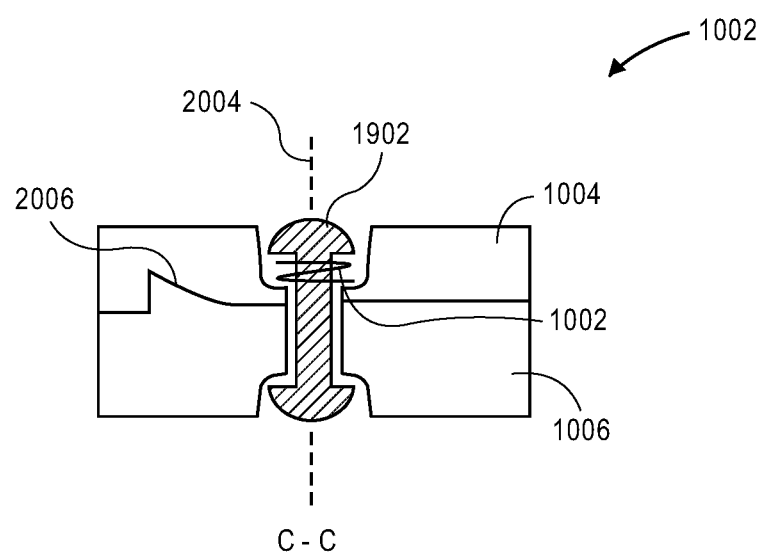

Referring to FIGS. 20A-20B, various views of a loading tool having spring-loaded pivoting body portions are shown in accordance with an embodiment. Referring to FIG. 20A, the body portions can be connected to each other by the hinge pin 1902, as described above with respect to FIGS. 19A-19D. The body portions can include recesses corresponding to the funnel and the loading volume 1021 for receiving the biostimulator 100 and the catheter. In an embodiment, the loading tool 1002 includes an interlocking clasp 1906 at the proximal end, as described above, to maintain the body portion halves in the closed configuration such that the funnel is formed by the interlocked halves.

Referring to FIG. 20B, a cross-sectional view taken about line C-C of FIG. 20A shows the spring-loaded pivoting body portions. In an embodiment, a spring 2002 is mounted on the hinge pin 1902. The spring 2002 can have a first end that acts against the hinge pin 1902 and a second end that acts against one of the body portions. For example, the top end of the spring 2002 can press against a head of the hinge pin 1902, and a bottom end of the spring 2002 can press against the first body portion 1004. More particularly, the first body portion 1004 can include a counterbore within which the hinge pin 1902 and the spring 2002 are mounted. The spring 2002 can act against a bottom surface of the counterbore. Similarly, the second body portion 1006 can include a bore within which another head of the hinge pin 1902 is mounted. A channel can extend between the bore and the counterbore, and thus, the hinge pin 1902 can extend along the channel through the first body portion 1004 and the second body portion 1006. The hinge pin 1902 can constrain transverse movement of the body portions about the pivot axis 2004, and the heads of the hinge pin 1902 can constrain vertical movement of the body portions. The heads constrain vertical movement because the heads resist movement of the body portions in the vertical direction beyond a length of the hinge pin 1902.

The spring 2002 can act upward on the hinge pin 1902 to move the top head of the hinge pin 1902 away from the bottom surface of the counterbore. As the hinge pin 1902 is pushed upward, the lower head of the hinge pin 1902 can act in an upward direction on the second body portion 1006. Accordingly, the spring 2002 can bias the second body portion 1006 toward the first body portion 1004. The first body portion 1004 and the second body portion 1006 can be clamped together by the spring action to secure the body portion halves against each other in the closed configuration.

In an embodiment, the loading tool 1002 includes a feature that separates the first body portion 1004 from the second body portion 1006 in the vertical direction when the body portions are pivoted about the pivot axis 2004 relative to each other. The loading tool 1002 can include a ramp 2006 feature such that, when the first body portion 1004 is rotated about the pivot axis 2004 relative to the second body portion 1006, the ramp 2006 guides the first body portion 1004 in a vertical direction. As the first body portion 1004 slides over the ramp 2006, the spring 2002 is compressed and the opposing surfaces of the body portions separate. A separation between the body portions can allow the first body portion 1004 to clear the biostimulator 100 as the body portion is swung open. For example, the ramp 2006 can have a height that is approximately equal to a transverse radius of the biostimulator 100. Accordingly, when the first body portion 1004 reaches an apex of the ramp 2006, the spring 2002 is compressed by a distance approximately equal to the clearance height between the second body portion 1006 and the highest point on the biostimulator 100, and the first body portion 1004 will clear the highest point. That is, when the first body half is rotated about the pivot axis 2004, the body half will ramp up and over the biostimulator 100 while being supported by the hinge pin 1902 with the spring action. When the first body portion 1004 clears the biostimulator 100, it can move to the open configuration to allow the user to remove the loading tool 1002 from the biostimulator 100 and the catheter.

The loading tool 1002 and biostimulator systems 1000 described above can be used to perform a method of loading a biostimulator 100 onto a biostimulator delivery system 300. A biostimulator system 1000 can be packaged with the biostimulator 100 contained in the loading tool 1002. The packaged system can be presented to the operator, e.g., a cardiovascular interventionist in a catheterization lab, when the loading tool 1002 is in the closed and locked state.

In an embodiment, the operator inserts a biostimulator delivery system 300 into the loading tool 1002. For example, the operator can hold the biostimulator delivery system 300 in a left hand and hold the loading tool 1002 in a right hand. The operator can bring the hands together to insert the docking cap 402 into the catheter volume 1023 of the loading tool 1002. As the docking cap 402 advances into the catheter volume 1023, one or more of the tethers of the biostimulator delivery system 300 can pass through the funnel volume 1024 of the loading tool 1002 into the opening 110 of the docking button 108. The distal ends 1016 of the tethers can pass through the opening 110 sequentially to connect the tethers to the biostimulator 100.

The operator can then use a one-handed opening method to remove the loading tool 1002 from the biostimulator 100. In an embodiment, while still holding the biostimulator delivery system 300 in the left hand, the operator can unlatch the latch of the loading tool 1002 with the right hand. More particularly, the operator can unlock the latch that is mounted on the first body portion 1004 by moving the latch 1202 relative to the first body portion 1004. The latch fastens the first body portion 1004 to the second body portion 1006, and thus, unlocking the latch can disengage the body portions from each other. The unlocking can be performed single-handedly, e.g., by the right hand of the operator while holding the biostimulator delivery system 300 with the left hand.

Simultaneous with or after the unlocking, the operator can swing the first body portion 1004 about the hinge 1008 to open the loading volume 1021 of the loading tool 1002. For example, by pinching or flipping the wing tabs 1304 of the loading tool 1002, the body portions can separate the body portions to cause the catheter volume 1023 and/or the funnel volume 1024 to open.

When the loading volume 1021 is opened, the loading tool 1002 can be removed from the biostimulator 100 and the biostimulator delivery system 300. The loading process can be performed while the operator continuously holds the biostimulator delivery system 300 in the left hand, and thus, a likelihood of damage to the tethers can be reduced because the biostimulator delivery system 300 remains supports by the hand and/or the guide barrel 1104 throughout the loading process.

The loading tool 1002 can include other features understood by one skilled in the art. For example, the loading tool 1002 may be formed of materials, e.g., plastics, metals, ceramics, that are acceptable for medical device applications. In an embodiment, the loading tool body portions are formed from one or more of clear polycarbonate or acetal. Portions of the loading tool 1002, such as hinges and/or hinge pins of the loading tool 1002, may be formed from metal, e.g., stainless steel. The materials can be sterilizable. The loading tool 1002 and method allows a single biostimulator delivery system 300 to be reused as needed for the implantation of multiple biostimulators 100.

Figure 21A:
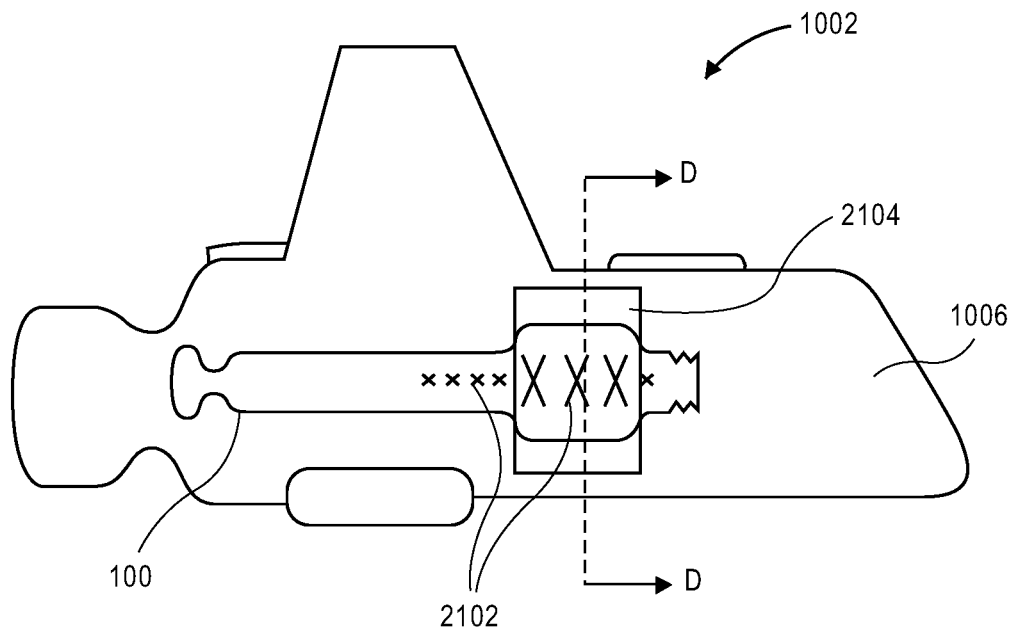
FIGS. 21A-21B are various views of a loading tool having a magnifier, in accordance with an embodiment.

Referring to FIG. 21A, a top view of a loading tool having a magnifier is shown in accordance with an embodiment. At least a portion of the loading tool 1002 can be transparent. For example, the second body portion 1006 can be formed from clear polycarbonate or acetal, and thus, the biostimulator 100 stored within the loading tool 1002 can be visible to a viewer through the second body portion 1006. In an embodiment, the biostimulator 100 includes markings on an outer surface. The markings can include text 2102, such as alphanumeric text 2102 constituting a serial number or other information corresponding to the biostimulator 100. For example, the serial number can identify the biostimulator 100 as having a certain size, model, manufacturing lot, etc., which the user can confirm prior to implantation of the device.

The text 2102 that is marked, e.g., printed or laser etched, on the outer surface of the biostimulator 100 may have a font or size that is small. Furthermore, the user may be attempting to read the text in a dim environment. Thus, it may be challenging to read the text. To increase the readability of the text 2102, the loading tool 1002 may include a magnifier 2104 that magnifies at least a portion of the text 2102 marked on the device. The magnifier 2104 can be, for example, a convex protrusion on the second body portion 1006 that bends light from the marking in such a way that an image of the text 2102 is magnified or enlarged relative to the native text size. More particularly, the magnifier 2104 can be a magnification lens that can aid the user in reading and confirming the information stored on the biostimulator 100 in the form of text or other visible data markings.

Figure 21B:
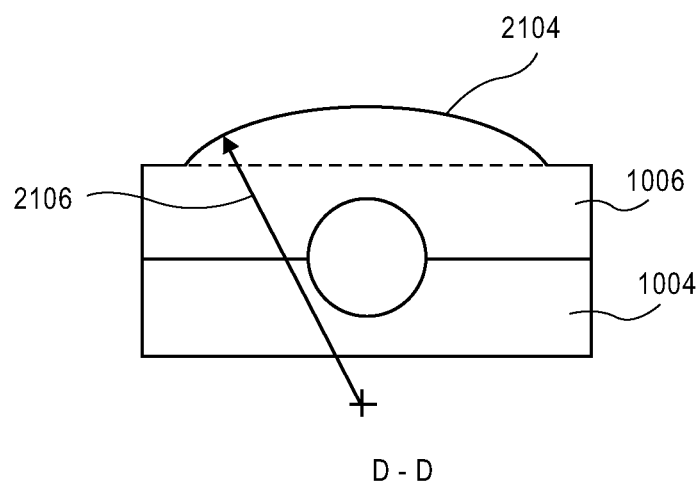

Referring to FIG. 21B, a cross-sectional view of a loading tool having a magnifier, taken about line D-D of FIG. 21A, is shown in accordance with an embodiment. In an embodiment, the magnifier 2104 is integral to a body portion of the biostimulator 100. For example, the magnifier 2104 may be a part of the second body portion 1006. More particularly, the magnifier 2104 can be a feature of the second body portion 1006 and be formed from the same native clear plastic material that is used to form the second body portion 1006. Alternatively, the magnifier 2104 may be a separate component that is mounted on the second body portion 1006. For example, the magnifier 2104 can include a lens that has a flat surface and a convex surface. The flat surface can be bonded to an outer surface of the second body portion 1006, which is represented by a horizontal dashed line in FIG. 21B.

In an embodiment, the magnifier lens has a convex outer surface facing away from the second body portion 1006. The convex outer surface can have a magnification radius 2106. The radius 2106 can be constant or can vary over a width of the magnifier 2104. More particularly, the radius 2106 can be selected to provide a desired amount of magnification of the text 2102 on the biostimulator 100.

Figure 22:
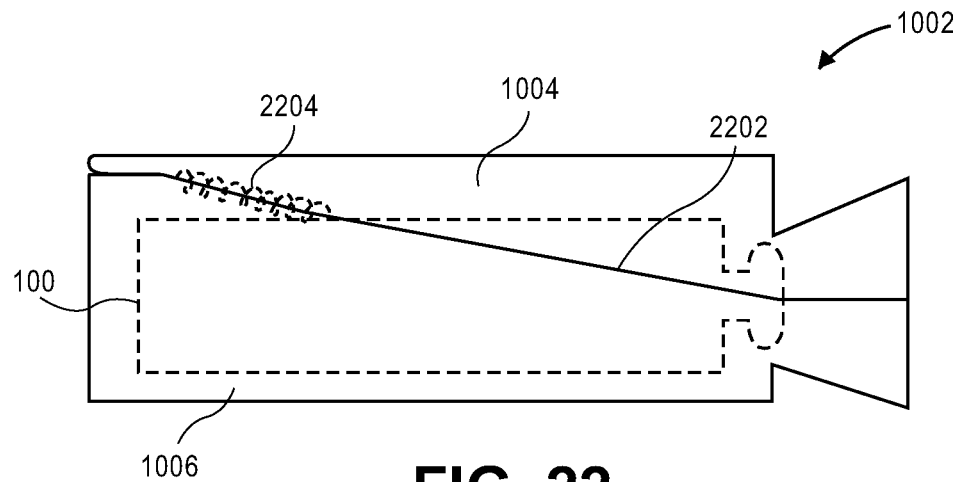
FIG. 22 is a side view of a multi-piece loading tool having a slide-action mechanism, in accordance with an embodiment.

Referring to FIG. 22, a side view of a multi-piece loading tool having a slide-action mechanism is shown in accordance with an embodiment. The loading tool 1002 can be a multi-piece system, e.g., a two-piece system, having the first body portion 1004 that is connected to the second body portion 1006 by a slide-action mechanism. More particularly, the first body portion 1004 can be connected to the second body portion 1006 by a slide 2202. The slide 2202 can include, for example, a track that has a tongue and groove connection between the body portions. The slide 2202 can provide a degree of freedom along an axis of the track. For example, the first body portion can slide backward from the closed configuration shown in FIG. 22 to an open configuration (FIG. 23B). The sliding action can result from a user applying a rearward pressure on an outer surface, e.g., a knurled surface or a tab 1904 (not shown), of the first body portion 1004 to cause the first body portion 1004 to move backward relative to the second body portion 1006.

In an embodiment, the slide 2202 is spring-loaded. For example, a spring 2004 can be loaded in a groove of the slide track. The spring 2204 can have a first end connected to the first body portion 1004 and a second end connected to the second body portion. The spring 2204 can be a compression or tension spring that stores energy when the body portions are moved relative to each other under the thumb action. By way of example, the spring 2204 can be a compression spring, and a distance between the spring ends can be greater in the closed configuration (FIG. 23A) than in the open configuration (FIG. 23B). The spring 2204 can therefore resists the backward motion of the first body portion 1004. The spring 2204 can bias the loading tool 1002 toward the closed configuration. For example, the spring 2204 can apply a return force to push the first body portion 1004 forward when the thumb action is removed.

Figure 23A:
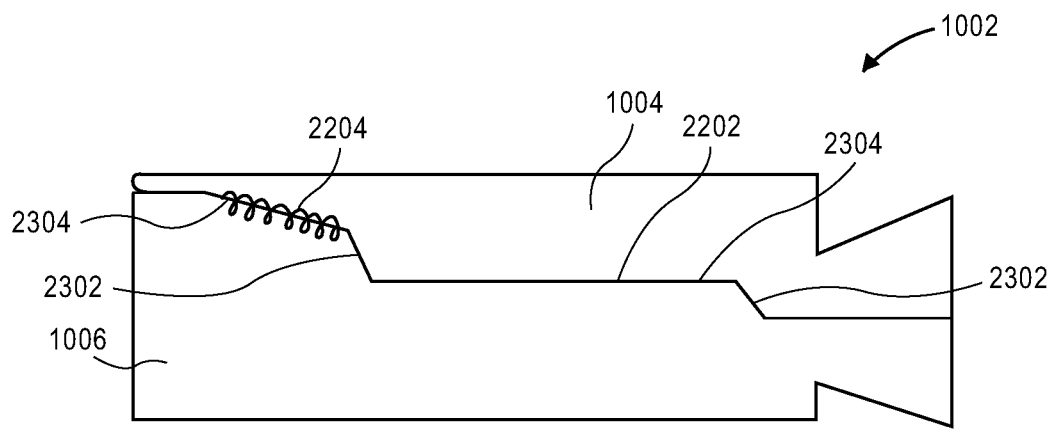
FIGS. 23A-23B are various views of a multi-piece loading tool having a slide-action mechanism in a closed configuration and an open configuration, in accordance with an embodiment.
Figure 23B:
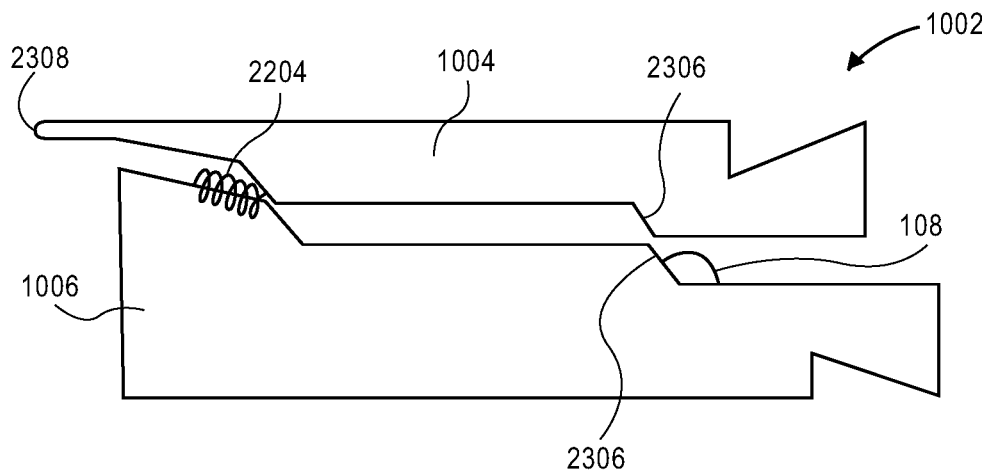

Referring to FIG. 23A, a multi-piece loading tool having a slide-action mechanism in a closed configuration is shown in accordance with an embodiment. The slide 2202 can have a single sloping track (FIG. 22). Alternatively, the slide 2202 can include several slide segments, each having a respective slope. In an embodiment, the slide 2202 includes one or more first slope segments 2302 and one or more second slope segments 2304. The first slope segments 2302 can have a larger angle relative to a horizontal plane extending through the biostimulator 100 than the second slope segments 2304. The slope segments can be formed as surface profiles in both body portions. More particularly, the surface profiles of the body portions 1004, 1006 can conform along the slope 2202 in the closed configuration to form a closed wall section of the loading tool 1002.

Referring to FIG. 23B, a multi-piece loading tool having a slide-action mechanism in an open configuration is shown in accordance with an embodiment. The first slope segments 2302 and the second slope segments 2304 can have a same or different slope steepness. For example, segments 2302 can be steeper than segments 2304 in the illustrated embodiment. The steeper slope of the first slope segments 2302 can allow the first body portion 1004, upon initiating the sliding action relative to the second body portion 1006, to lift up and over the docking button 108. That is, the sliding action can cause the body portions to separate such that the first body portion 1004 clears the biostimulator 100 to provide a path for the device to be removed from the loading tool. More particularly, as the slope segment surfaces 2306 at the first slope segment 2302 of the body portions ride over each other, the body portions will split apart, and the loading tool 1002 will move toward the open configuration having an open wall section. The rate of opening of the wall section will depend on the angle of the ramp that forms the slope segment surfaces 2306. In an embodiment, the angle of the ramp is sufficient to allow the biostimulator 100 to be removed from the loading tool 1002 in a forward direction through a gap between the first body portion 1004 and the second body portion 1006 when a front end of the slope segment surface 2306 of the first body portion 1004 meets a rear end of the slope segment surface 2306 of the second body portion 1106, as shown.

In an embodiment, the body portions 1004, 1006 can continue to slide relative to each other to open the loading tool further. For example, the slope segment surfaces 2306 can continue to move relative to each other such that the portion of the first body portion 1004 that began sliding on the first slope segment 2302 of the second body portion 1006 continues to slide backward onto the second slope segment 2304 of the second body portion 1006. The first body portion 1004 can slide rearward and continue to split apart from the second body portion 1006 until the first body portion 1004 clears the biostimulator 100. Accordingly, the FIG. 23B represents the loading tool in a partially slid back configuration to illustrate how the body portions interact with each other during the slide process, however, it will be understood that the tracks on the body portions can continue to interact and slide relative to each other to widen the opening for device removal.

In an embodiment, a rear edge 2308 of one or more of the body portions is blunted to avoid sharp edges. For example, first body portion 1004 can have a rounded, chamfered, or otherwise blunted rear edge 2308. When the rear edge 2308 moves backward relative to a rear wall of the second body portion 1006, the rear edge 2308 may be exposed. The blunted shape of the edge can reduce a likelihood that the exposed edge will cut a glove or another object in the operating arena.

Figure 24A:
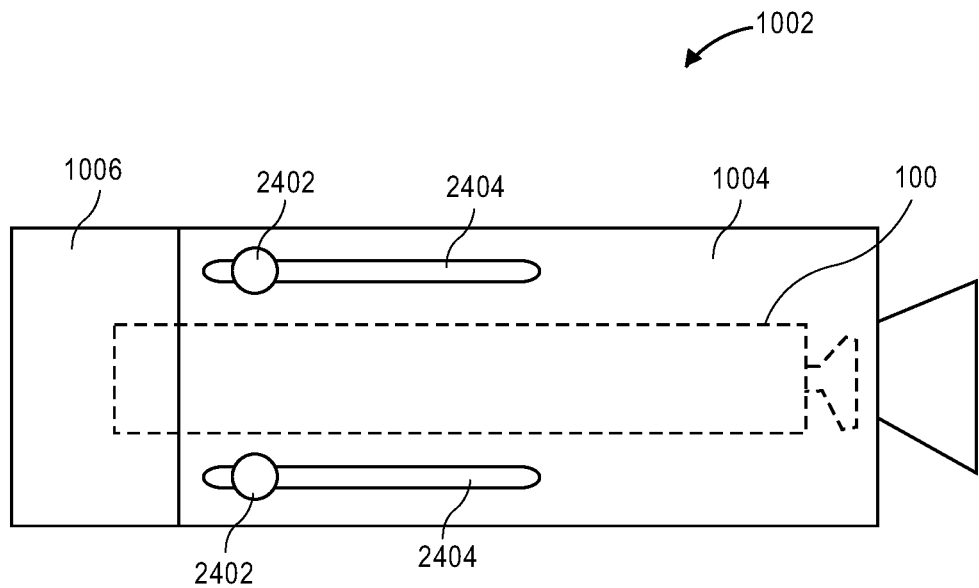
FIGS. 24A-24B are various views of a multi-piece loading tool including a slide-action mechanism having a spring-loaded pin, in accordance with an embodiment.

Referring to FIG. 24A, a top view of a multi-piece loading tool including a slide-action mechanism having a spring-loaded pin is shown in accordance with an embodiment. The loading tool 1002 having a multi-piece design can include the first body portion 1004 coupled to the second body portion 1006 by one or more pins 2402. The pins can be spring-loaded to bias the body portions toward the closed configuration, as described below. In an embodiment, each pin 2402 has a central barrel that rides within a respective slot 2404. For example, the slot 2404 can be formed in the first body portion 1004. The slot 2404 can have a longitudinal profile and length, and can include a proximal, or forward, slot end and a distal, or rearward, slot end. Accordingly, when the first body portion 1004 is urged forward or backward, the pin 2402 can ride within the slot 2404 until the barrel of the pin 2402 reaches one of the slot ends to stop the sliding action. The slots 2404 can have a width that allows for a sliding fit between the pin 2402 and the slot walls, and thus, the pin 2402 can prevent lateral motion of the body portions to maintain the body portions in lateral alignment.

Figure 24B:
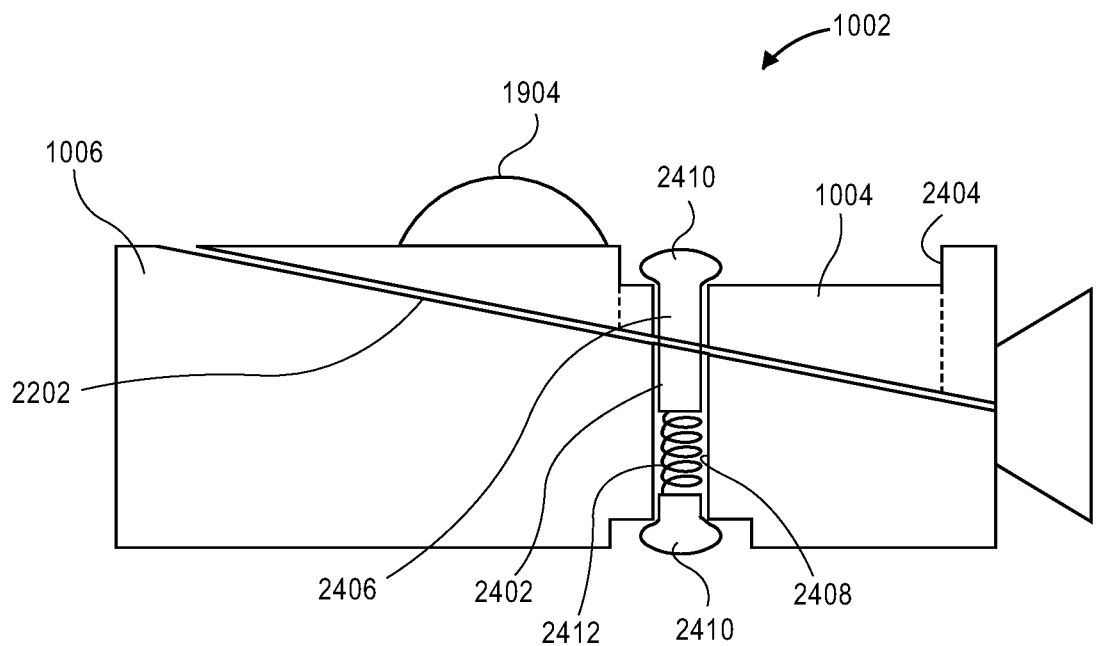

Referring to FIG. 24B, a side view of a multi-piece loading tool including a slide-action mechanism having a spring-loaded pin is shown in accordance with an embodiment. A barrel 2406 of the pin 2402 can extend through the slot 2404 and a transverse hole 2408. The slot and hole can extend through one or more of the body portions in the transverse, e.g., vertical, direction. The pin 2402 can be retained within the transverse hole 2408 and the slot 2404 by an upper and lower head 2410. The heads 2410 of the pin 2402 can have a larger diameter than the transverse hole 2408 to prevent the pins from sliding inward under the action of a spring 2412.

In an embodiment, the pin 2402 is a two-part pin having an upper portion with a head 2410 that engages the first body portion 1004 and a lower portion with a head 1410 that engages the second body portion 1006. The pin portions can be coupled to each other by the spring 2412, which can be a tension spring having ends coupled to respective portions of the pin 2402. Accordingly, the tension spring can pull the pin portions inward toward each other.

In an embodiment, the loading tool 1002 includes the slide 2202, e.g., a linear ramp as shown in FIG. 24B or a segmented ramp as described above, such that the first body portion 1004 can be moved backward when the user applies backward pressure to the first body portion 1004, e.g., by applying thumb pressure to the tab 1904. As the body portions move relative to each other, the spring 2412 can lengthen. More particularly, as the first body portion 1004 slides backward over the ramp relative the second body portion 1006, the head 2410 within the slot 2404 can slide forward to a thicker region of the first body portion 1004. The increased thickness of the sliding body portion increases a distance between the heads 2410, causing an elongation of the spring 2412. As the spring 2412 elongates, the pins 2402 maintain a transverse alignment of the body portions until the loading tool 1002 reaches the open configuration (not shown). The biostimulator 100 can be removed from the opened loading tool 1002. The spring force acting inward on the body portions can increase a friction between the body portions along the ramp, and thus, the body portions can remain in the open configuration until the user slides the tab 1904 forward to close the loading tool 1002.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A loading tool for loading a biostimulator onto a biostimulator delivery system, comprising:
   a first body portion;
   a latch slidably mounted on the first body portion and including a latch hook;
   a second body portion pivotally coupled to the first body portion at a hinge having a hinge axis, wherein the second body portion has a keeper including a keeper recess in an outer surface of the second body portion, wherein the keeper recess is exposed radially outward from the hinge axis through the outer surface, wherein the keeper recess has an L-shaped profile including a vertical section to receive the latch hook through the outer surface when the second body portion pivots about the hinge against the first body portion, wherein the L-shaped profile includes a horizontal section to lock the first body portion against the second body portion when the latch slides to move the latch hook from the vertical section into the horizontal section, and wherein the first body portion and the second body portion are on a first side of a plane containing the hinge axis when the latch fastens the first body portion to the second body portion; and
   a plurality of wing tabs extending outward from the first body portion and the second body portion on an opposite side of the plane from the first body portion and the second body portion, wherein a transverse plane orthogonal to the hinge axis intersects the plurality of wing tabs.

2. The loading tool of claim 1, wherein the first body portion includes a first recess in a first face, wherein the second body portion includes a second recess in a second face, and wherein the first recess and the second recess define a loading volume when the first face is apposed to the second face, the loading volume including:
   a biostimulator volume to receive the biostimulator,
   a catheter volume to receive the biostimulator delivery system, and
   a funnel volume tapering from the catheter volume to the biostimulator volume.

3. The loading tool of claim 2, wherein the first body portion and the second body portion form a neck around the funnel volume and a guide barrel around the catheter volume, and wherein the guide barrel extends proximally from the neck.

4. The loading tool of claim 3 further comprising a detent extending inward from the guide barrel.

5. The loading tool of claim 4, wherein the biostimulator delivery system includes a docking cap, and wherein when the docking cap is positioned in the catheter volume, the detent is located proximal to the docking cap to prevent proximal displacement of the docking cap relative to the neck.

6. The loading tool of claim 5, wherein the biostimulator delivery system includes a first tether and a second tether, wherein each tether includes a respective distal end axially displaceable relative to the docking cap, and wherein the biostimulator includes a docking button having an opening sized to receive one of the distal ends at a time.

7. A biostimulator system, comprising:
   a loading tool including a first body portion, a latch slidably mounted on the first body portion and including a latch hook, a second body portion pivotally coupled to the first body portion at a hinge having a hinge axis, wherein the second body portion has a keeper including a keeper recess in an outer surface of the second body portion, wherein the keeper recess is exposed radially outward from the hinge axis through the outer surface, wherein the keeper recess has an L-shaped profile including a vertical section to receive the latch hook through the outer surface when the second body portion pivots about the hinge against the first body portion, wherein the L-shaped profile includes a horizontal section to lock the first body portion against the second body portion when the latch slides to move the latch hook from the vertical section into the horizontal section, and wherein the first body portion and the second body portion are on a first side of a plane containing the hinge axis when the latch fastens the first body portion to the second body portion, and a plurality of wing tabs extending outward from the first body portion and the second body portion on an opposite side of the plane from the first body portion and the second body portion, wherein the first body portion and the second body portion include respective recesses that combine to form a loading volume, and wherein a transverse plane orthogonal to the hinge axis intersects the plurality of wing tabs; and a biostimulator mounted in the loading volume, wherein the biostimulator includes an anchor mounted on a housing, and a docking button having an opening.

8. The biostimulator system of claim 7, wherein the first body portion includes a first recess in a first face, wherein the second body portion includes a second recess in a second face, and wherein the first recess and the second recess define the loading volume when the first face is apposed to the second face, the loading volume including:

a biostimulator volume to receive the biostimulator, a catheter volume to receive a biostimulator delivery system, and a funnel volume tapering from the catheter volume to the biostimulator volume.

9. The biostimulator system of claim 8, wherein the first body portion and the second body portion form a neck around the funnel volume and a guide barrel around the catheter volume, and wherein the guide barrel extends proximally from the neck.

10. The biostimulator system of claim 9 further comprising a detent extending inward from the guide barrel.

11. The biostimulator system of claim 10, wherein the biostimulator delivery system includes a docking cap, and wherein when the docking cap is positioned in the catheter volume, the detent is located proximal to the docking cap to prevent proximal displacement of the docking cap relative to the neck.

12. The biostimulator system of claim 11, wherein the biostimulator delivery system includes a first tether and a second tether, wherein each tether includes a respective distal end axially displaceable relative to the docking cap, and wherein the opening of the docking button is sized to receive one of the distal ends at a time.

13. A method of loading a biostimulator onto a biostimulator delivery system, comprising:

inserting a docking cap of the biostimulator delivery system into a catheter volume of a loading tool, wherein one or more tethers of the biostimulator delivery system pass through a funnel volume of the loading tool into an opening of the biostimulator when the docking cap is inserted into the loading tool;

unlocking a latch of the loading tool, wherein the latch is slidably mounted on a first body portion of the loading tool and includes a latch hook, wherein a second body portion of the loading tool is pivotally coupled to the first body portion at a hinge having a hinge axis, wherein the second body portion has a keeper including a keeper recess in an outer surface of the second body portion, wherein the keeper recess is exposed radially outward from the hinge axis through the outer surface, wherein the keeper recess has an L-shaped profile including a vertical section to receive the latch hook through the outer surface when the second body portion pivots about the hinge against the first body portion, wherein the L-shaped profile includes a horizontal section to lock the first body portion against the second body portion when the latch slides to move the latch hook from the vertical section into the horizontal section, and wherein the first body portion and the second body portion are on a first side of a plane containing the hinge axis when the latch fastens the first body portion to the second body portion;

pinching a plurality of wing tabs to swing the first body portion about the hinge that holds the first body portion to the second body portion to open the catheter volume and the funnel volume of the loading tool, wherein the plurality of wing tabs extend outward from the first body portion and the second body portion on an opposite side of the plane from the first body portion and the second body portion, and wherein a transverse plane orthogonal to the hinge axis intersects the plurality of wing tabs; and removing the loading tool from the biostimulator and the biostimulator delivery system.

14. The method of claim 13, wherein unlocking the latch is performed single-handedly.

\* \* \* \* \*